(12) United States Patent
di Tomaso et al.

(10) Patent No.: US 10,434,092 B2
(45) Date of Patent: Oct. 8, 2019

(54) DOSAGE REGIMEN FOR AN ALPHA-ISOFORM SELECTIVE PHOSPHATIDYLINOSITOL 3-KINASE INHIBITOR

(71) Applicant: Novartis AG, Basel (CH)

(72) Inventors: Emmanuelle di Tomaso, Lexington, MA (US); Marie-Caroline Germa, Croissy-sur-Seine (FR); Cristian Massacesi, Neuilly-sur-Seine (FR); Christine Fritsch, Steinbach (FR); Christian René Schnell, Hegenheim (FR); Ranjana Tavorath, Basking Ridge, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/719,636

(22) Filed: Sep. 29, 2017

(65) Prior Publication Data

US 2018/0078540 A1    Mar. 22, 2018

Related U.S. Application Data

(63) Continuation of application No. 15/101,155, filed as application No. PCT/IB2014/066558 on Dec. 3, 2014, now abandoned.

(30) Foreign Application Priority Data

Dec. 6, 2013 (EP) .................... 13306679

(51) Int. Cl.
*A61K 31/4439* (2006.01)
*A61K 9/00* (2006.01)

(52) U.S. Cl.
CPC ........ *A61K 31/4439* (2013.01); *A61K 9/0053* (2013.01)

(58) Field of Classification Search
CPC .......................... A61K 31/4439; A61K 9/0053
See application file for complete search history.

(56) References Cited

U.S. PATENT DOCUMENTS 6,429,224 B1   8/2002  Calabresi et al.
8,227,462 B2   7/2012  Fairhurst et al.

FOREIGN PATENT DOCUMENTS

| WO | 2010/029082 A1 | 3/2010 |
|---|---|---|
| WO | 2013173283 A1 | 11/2011 |
| WO | 2012/062694 A1 | 5/2012 |
| WO | 2012175522 A1 | 12/2012 |

OTHER PUBLICATIONS

Duric et al. Cancer research Supp 72(24) 2012.*
A M Gonzalez-Angulo: "Safety, pharmacokinetics, and preliminary activity of the [alpha]-specific PI3K inhibitor BYL719: results from the first-in-human study", May 31, 2013 (May 31, 2013), 2013 ASCO Annual Meeting; XP055114130, retrieved from the Internet: URL:htt;://meetinglibrary.asco.org/content/114843-132.
Furet Pascal et al: "Discovery of NVP-BYL719 a potent and selective phosphatidylinositol-3 kinase alpha inhibitor selected for clinical evaluation", Biorganic & Medician Chemistry Letters, Pergamon, Amsterdam, NL., vol. 23, No. 13, May 14, 2013 (May 14, 2013), pp. 3741-3748, XP028564917.
NIH Guidelines for Treatment Regimens, National Cancer Institute, 2008.
Juric D. Abstract P6-10-07: Phase I study of BYL719, an alpha-specific PI3K inhibitor, in patients with PIK3CA mutant advanced solid tumors: preliminary efficacy and safety in patients with PIK3CA mutant ER-positive (ER+) metastatic breast cancer (MBC). American Association for Cancer Research. vol. 72, Issue 24 Supplement, pp. P6-10-07.

* cited by examiner

*Primary Examiner* — Shirley V Gembeh
(74) *Attorney, Agent, or Firm* — Scott W. Reid

(57) ABSTRACT

The present invention relates to methods of treating or preventing a proliferative disease in a patient in need thereof by orally administering a therapeutically effective amount of an alpha-isoform selective phosphatidylinositol 3-kinase inhibitor compound of formula (I) or a pharmaceutically acceptable salt thereof for at least two five-consecutive day cycle, wherein said compound is not administered to the patient for a period of about two days to about three days between said five-consecutive day cycles; the use of said compound of formula (I) or a pharmaceutically acceptable salt thereof for the manufacture of a medicament for treating or preventing a proliferative disease administered in accordance with said dosage regimen; therapeutic regimen comprising administration of said compound of formula (I) or a pharmaceutically acceptable salt thereof in accordance with said dosage regimen; and related pharmaceutical compositions and packages thereof.

5 Claims, 15 Drawing Sheets

Fig. 1
Fig. 1A
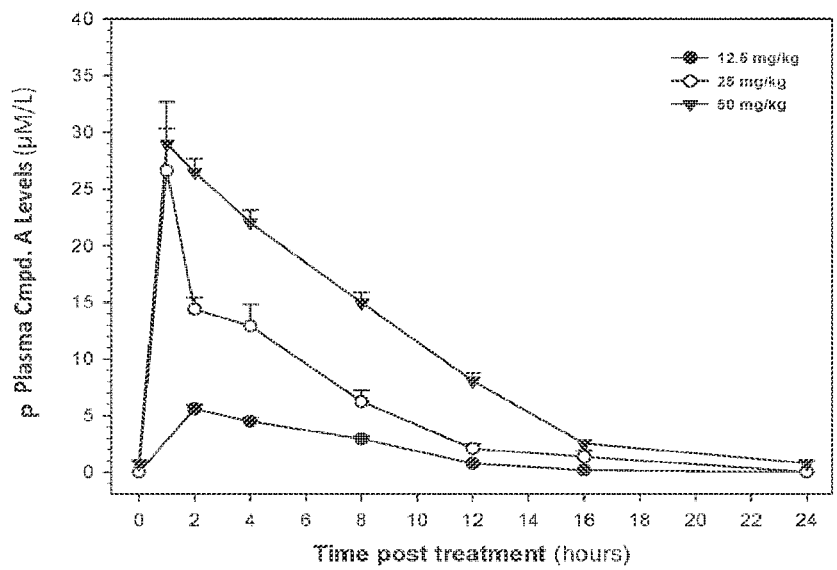
Fig. 1B
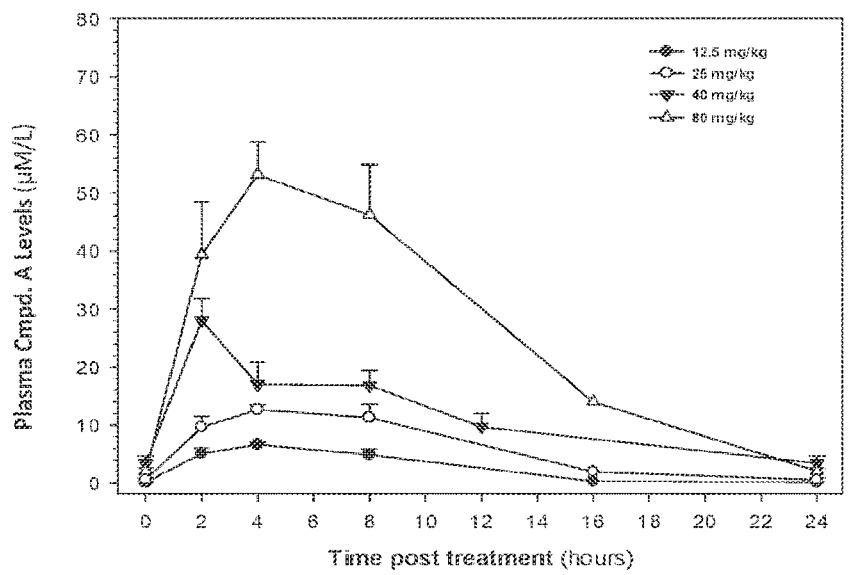

Fig. 2
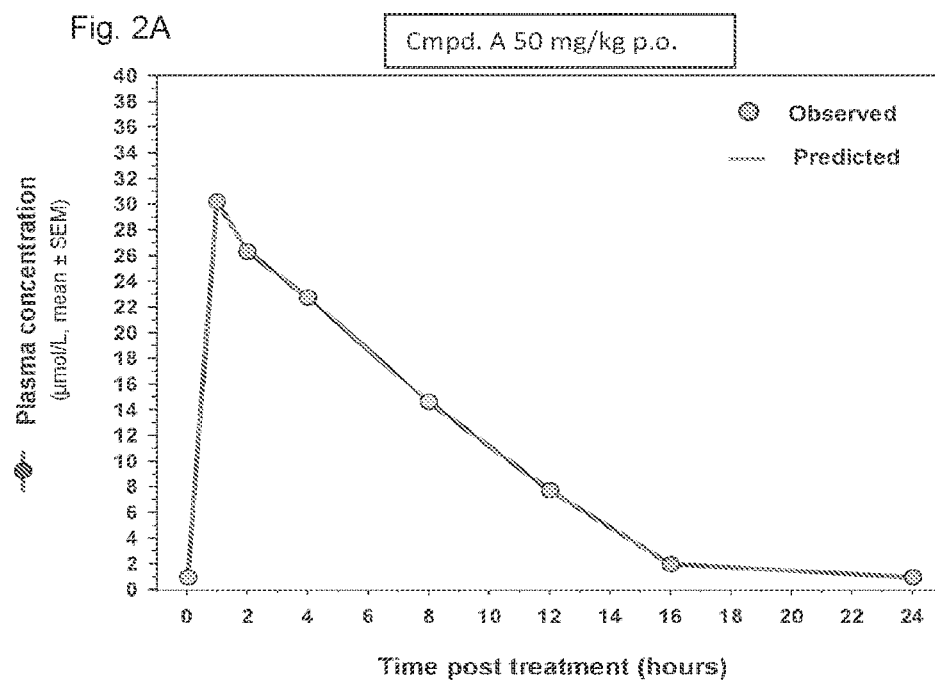
Fig. 2A
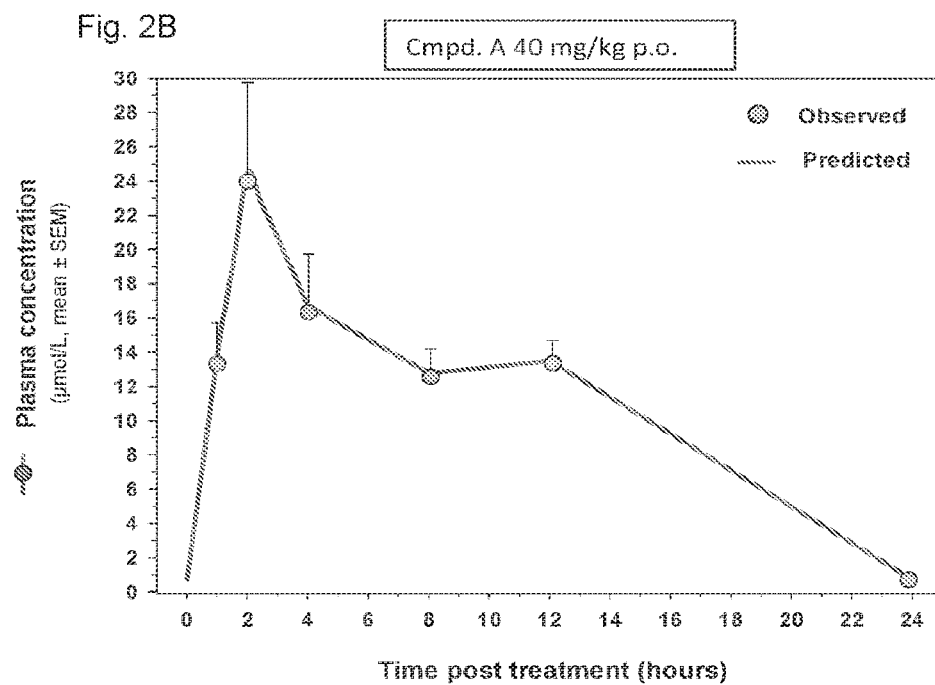
Fig. 2B

Fig. 3
Fig. 3A
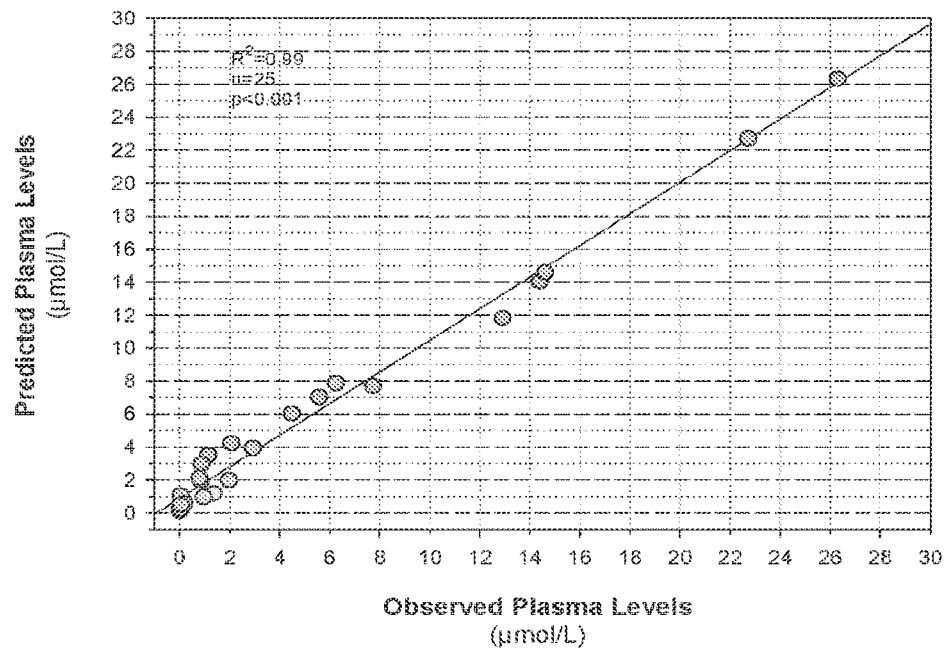
Fig. 3B
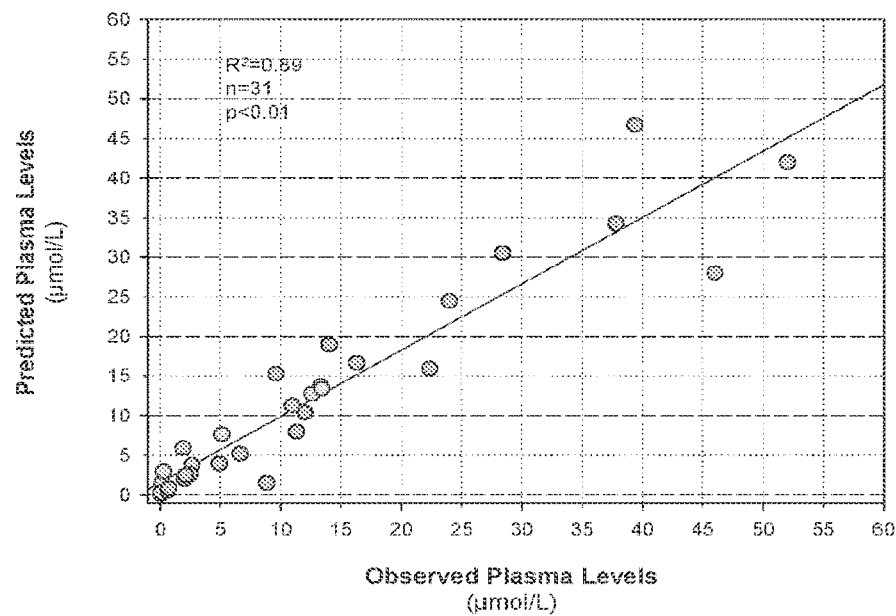

Fig. 4
Fig. 4A
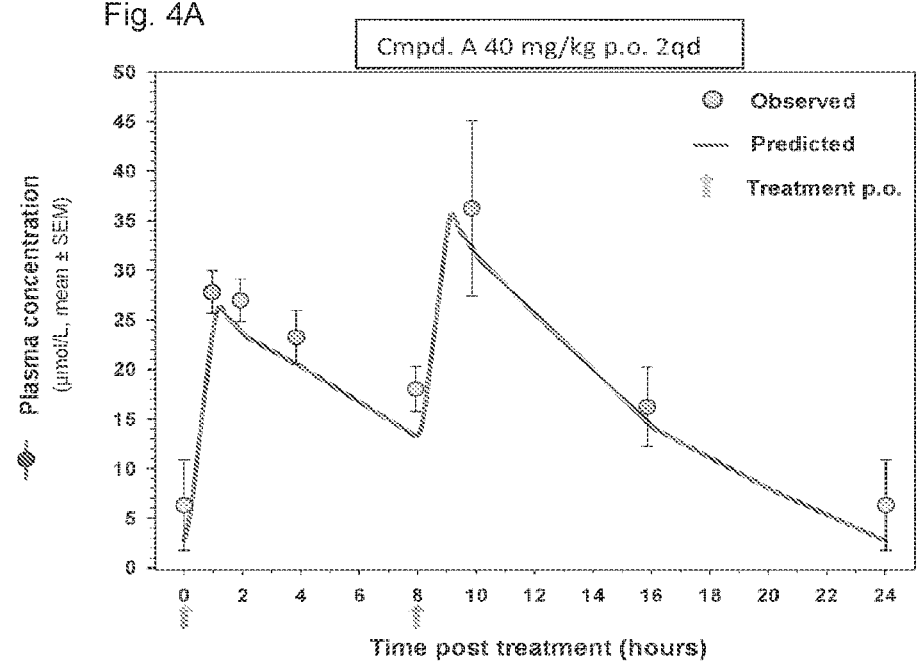
Fig. 4B
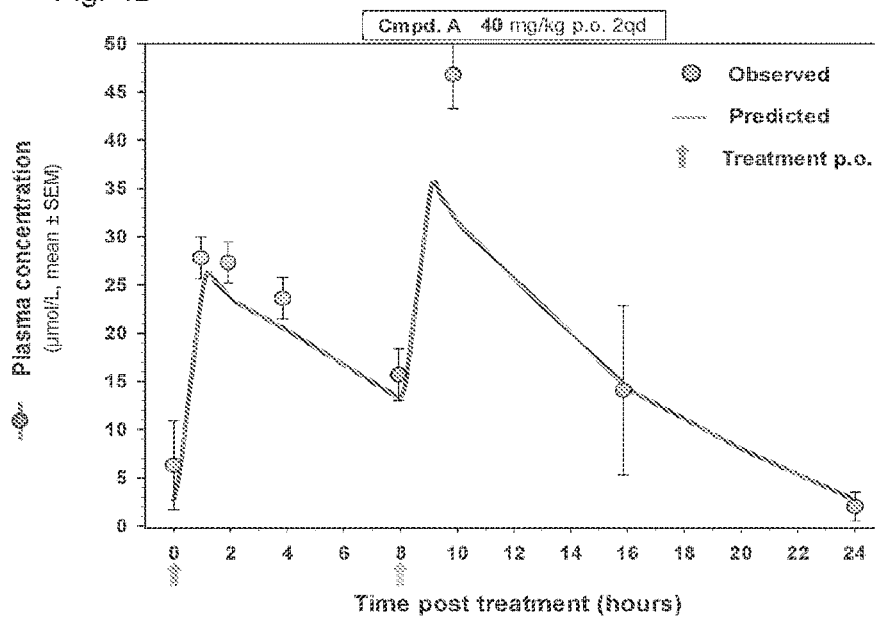

Fig. 9
Fig. 9A
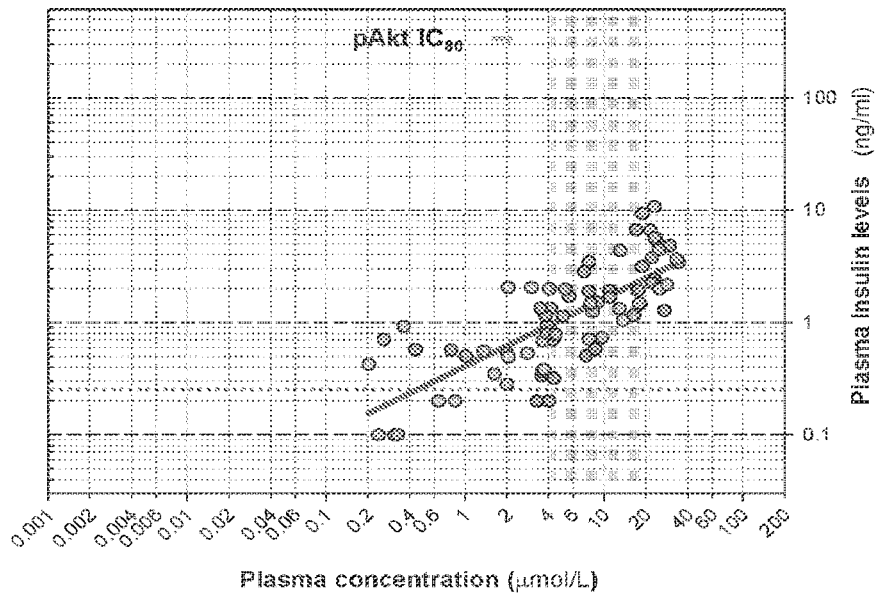
Fig. 9B
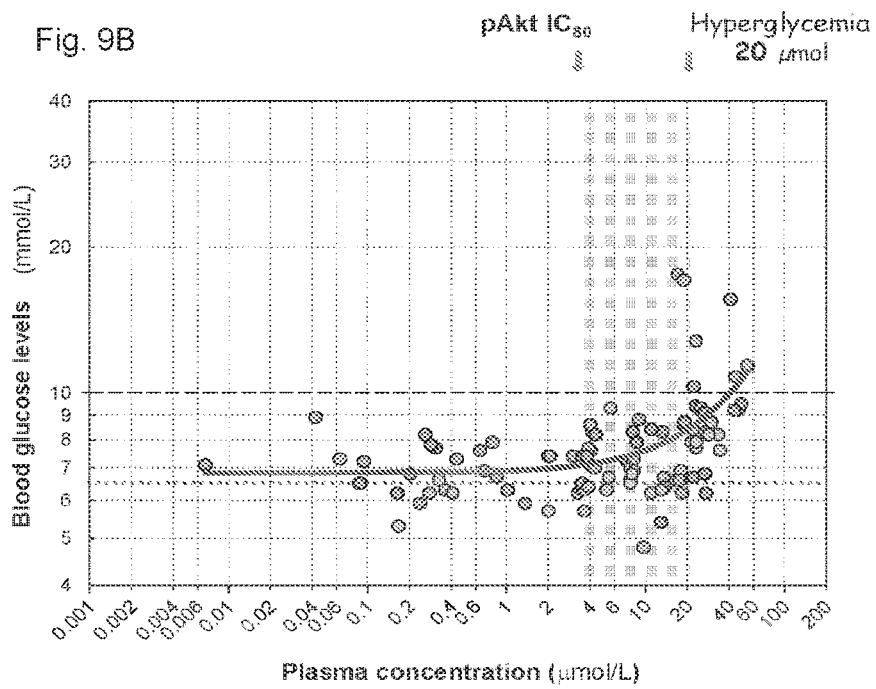

Fig. 10
Fig. 10A
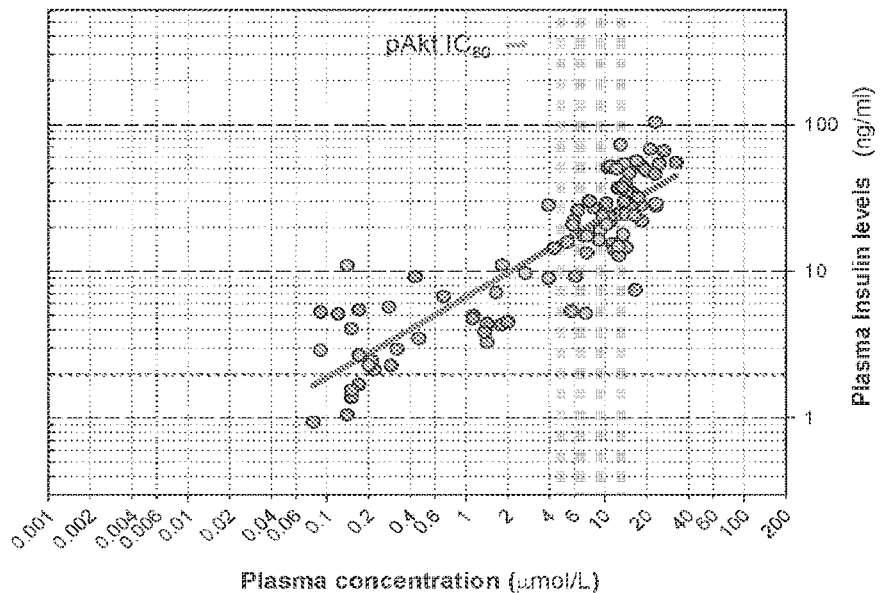
Fig. 10B
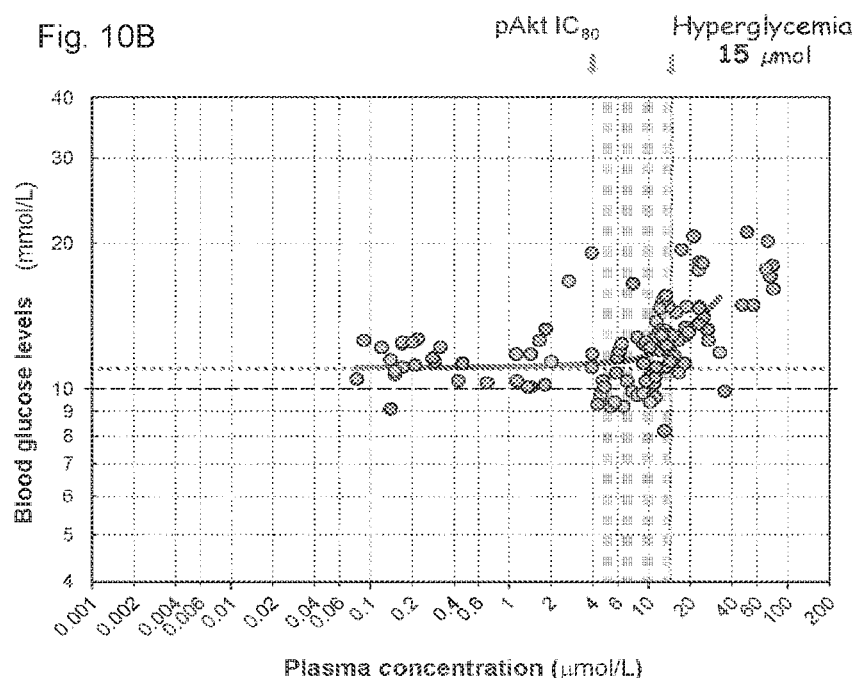

Fig. 14
Fig. 14A
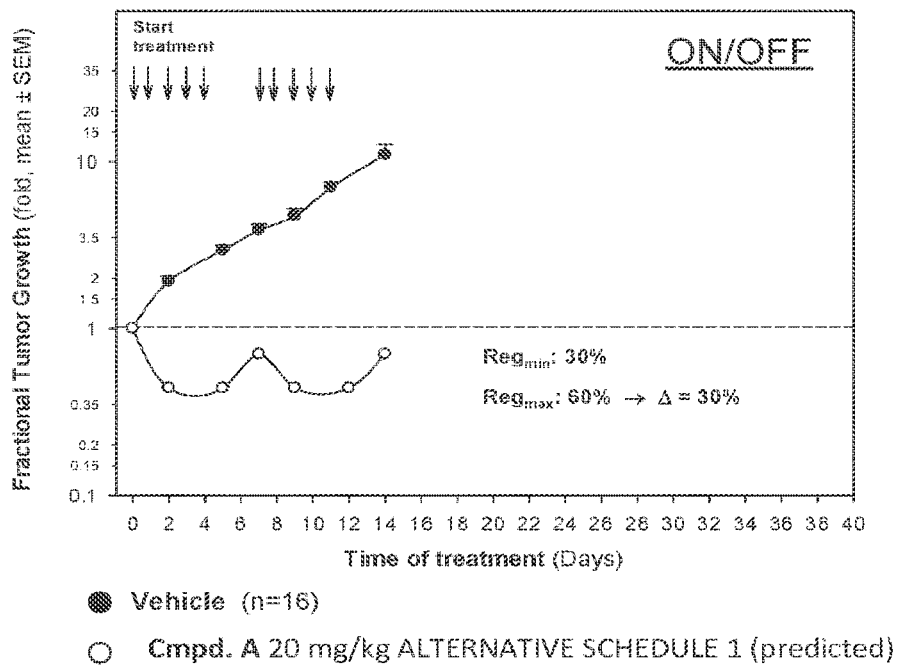
● Vehicle (n=16)
○ Cmpd. A 20 mg/kg ALTERNATIVE SCHEDULE 1 (predicted)
Fig. 14B
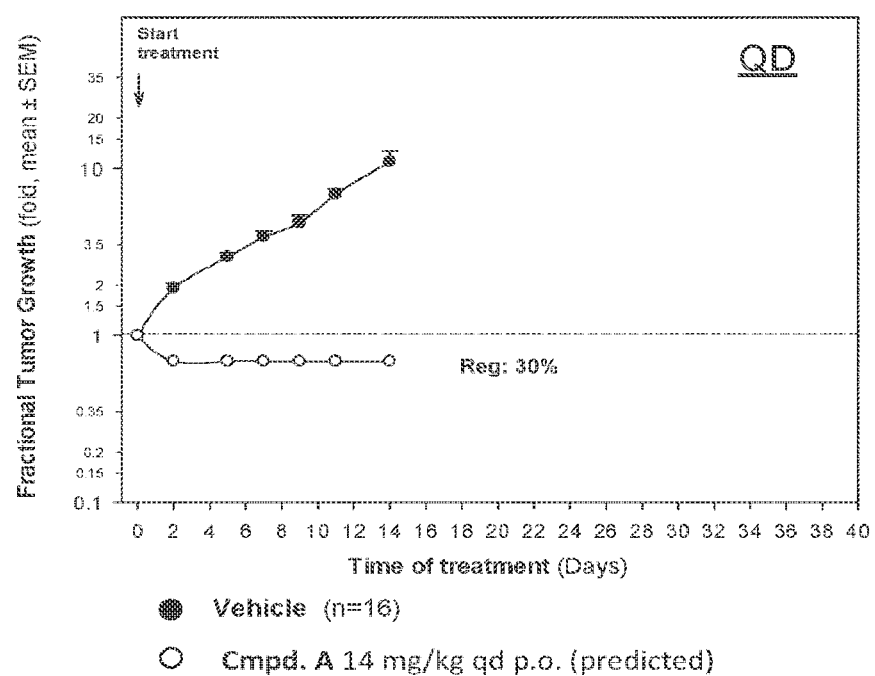
● Vehicle (n=16)
○ Cmpd. A 14 mg/kg qd p.o. (predicted)

DOSAGE REGIMEN FOR AN ALPHA-ISOFORM SELECTIVE PHOSPHATIDYLINOSITOL 3-KINASE INHIBITOR

FIELD OF THE INVENTION

The present invention relates to methods of treating or preventing a proliferative disease in a patient in need thereof by orally administering a therapeutically effective amount of an alpha-isoform selective phosphatidylinositol 3-kinase inhibitor compound of formula (I) or a pharmaceutically acceptable salt thereof to the patient for at least two five-consecutive day cycles, wherein said compound or a pharmaceutically acceptable salt thereof is not administered to the patient for a period of about two days to about three days between said five-consecutive day cycles; the use of said compound of formula (I) or a pharmaceutically acceptable salt thereof for the manufacture of a medicament for treating or preventing a proliferative disease administered in accordance with said dosage regimen; therapeutic regimen comprising administration of said compound of formula (I) or a pharmaceutically acceptable salt thereof in accordance with said dosage regimen; and related pharmaceutical compositions and packages thereof.

BACKGROUND OF THE INVENTION

Phosphatidylinositol 3-kinases ("PI-3 kinase" or "PI3K") comprise a family of lipid kinases that catalyze the transfer of phosphate to the D-3' position of inositol lipids to produce phosphoinositol-3-phosphate ("PIP"), phosphoinositol-3,4-diphosphate ("PIP2") and phosphoinositol-3,4,5-triphosphate ("PIP3") that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., Annu. Rev. Biochem 70:535 (2001); Katso et al., Annu. Rev. Cell Dev. Biol. 17:615 (2001)). Human cells contain three genes (PIK3CA, PIK3CB and PIK3CD) encoding the catalytic p110 subunits (α, β, δ isoforms) of class IA PI3K enzymes. These catalytic p110α, p110β, and p110δ subunits are constitutively associated with a regulatory subunit that can be p85α, p55α, p50α, p85β or p55γ. p110α and p110β are expressed in most tissues. Class 1B PI3K has one family member, a heterodimer composed of a catalytic p110γ subunit associated with one of two regulatory subunits, either the p101 or the p84 (Fruman et al., Annu Rev. Biochem. 67:481 (1998); Suire et al., Curr. Biol. 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B, as well as p110β in some circumstances, is activated directly by G protein-coupled receptors that bind a diverse repertoire of peptide and non-peptide ligands (Stephens et al., Cell 89:105 (1997)); Katso et al., Annu. Rev. Cell Dev. Biol. 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., Cell 64:281 (1991); Escobedo and Williams, Nature 335:85 (1988); Fantl et al., Cell 69:413 (1992)).

Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110a isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers, including 32% of colorectal cancers, 27% of glioblastomas, 25% of gastric cancers, 36% of hepatocellular carcinomas, and 18-40% of breast cancers. (Samuels et al., Cell Cycle 3(10):1221 (2004); Hartmann et al, Acta Neuropathol., 109(6):639 (June 2005); Li et al, BMC Cancer 5:29 (March 2005); Lee et al, Oncogene, 24(8):1477 (2005); Backman et al, Cancer Biol. Ther. 3(8): 772-775 (2004); Campbell et al., Cancer Research, 64(21): 7678-7681 (2004); Levine et al., Clin. Cancer Res., 11(8): 2875-2878 (2005); and Wu et al, Breast Cancer Res., 7(5):R609-R616 (2005)). Deregulation of PI3K, including the α-isoform, is one of the most common deregulations associated with human cancers and proliferative diseases (Parsons et al., Nature 436:792 (2005); Hennessey at el., Nature Rev. Drug Disc. 4:988-1004 (2005)).

(S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) is a specific 2-carboxamide cycloamino urea derivative compound that potently and selectively targets the alpha (α)-isoform of class IA PI3K. This compound has the following chemical structure:

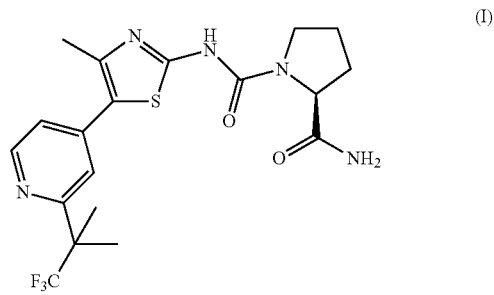 [SMILES: Cc1nc(NC(=O)N2CCC[C@H]2C(N)=O)sc1-c1ccnc(C(C)(C)C(F)(F)F)c1]

(hereinafter, "compound of formula (I)" or "Compound A"). The compound of formula (I) and pharmaceutically acceptable salts thereof, suitable formulations, and its method of preparation are described in PCT Application WO2010/029082.

In a Phase I clinical trial, this alpha-isoform selective PI3K inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) demonstrated clinical efficacy in the single-agent treatment of patients having advanced solid malignancies carrying an alteration in the PIK3CA gene. In the dose escalation phase, patients were orally administered this compound either (a) at a dosage ranging from 30 mg to 450 mg once per day (q.d.) on a continuous daily schedule for 28-days, or (b) at a dosage ranging from 120 mg to 200 mg twice per day (b.i.d.)

on a continuous daily schedule for 28-days, as guided by Bayesian logistic regression model with overdose control. After determination of the maximal tolerated dose (MTD), the dose expansion phase was conducted to additionally treat patients having head and neck cancer with a PIK3CA alteration, patients having solid tumors with PIK3CA alteration, and patients having PIK3CA wildtype ER+/HER2- breast cancer. Clinical efficacy of this compound has been demonstrated preliminarily. As of Feb. 15, 2013, confirmed partial responses have been observed in several patients treated at ≥270 mg/day, including patients suffering from breast cancer (1 patient, confirmed), colorectal cancer (1 patient confirmed), endometrial cancer (1 patient, confirmed) and cervical cancer (1 patient confirmed). (Gonzalez-Angulo et al., "Safety, pharmacokinetics, and preliminary activity of the α-specific PI3K inhibitor BYL719: results from the first-in-human study", Presentation at the 2013 ASCO Annual Meeting, held May 31-Jun. 4, 2013 in Chicago, Ill.)

Despite the clinical efficacy of this compound in this Phase I clinical trial, some patients administered this compound on the once per day or twice per day continuous daily schedule demonstrated at least one side effect or adverse event including, but not limited to, hyperglycemia (49% of patients), nausea (43% of patients), decreased appetite (34% of patients), diarrhea (35% of patients), rash and hypersensitivity (34% of patients), asthenia/fatigue (34% of patients), vomiting, stomatitis, dysgeusia, and/or dyspepsia. (Gonzalez-Angulo et al., Presentation at the 2013 ASCO Annual Meeting, held May 31-Jun. 4, 2013 in Chicago, Ill.)

Currently, there is an unmet need for a potent alpha (α)-isoform selective PI3K inhibitor which can be administered to patients in a dosage or dosage regimen that is clinically effective for treatment of proliferative diseases, particularly cancer, but also that relieves, reduces, or alleviates the any known and unknown side effects (e.g, by severity, occurrence rate, or frequency) of the drug. It is believed that this has not been achieved for any alpha-isoform selective PI3K inhibitor prior to the present invention.

SUMMARY OF THE INVENTION

The present invention relates to a method of treating or preventing a proliferative disease in a patient in need thereof, comprising orally administering a therapeutically effective amount of the compound of formula (I):

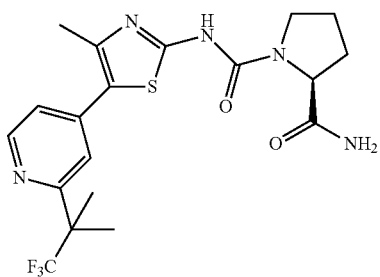

or a pharmaceutically acceptable salt thereof to the patient in a daily dose of about 100 mg to about 450 mg for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to a method of treating or preventing a proliferative disease comprising first administering to a patient in need thereof a compound of formula (I) or a pharmaceutically acceptable salt thereof in amount of about 100 mg to about 450 mg daily on a continuous daily schedule via oral administration, second determining said patient has a side effect selected from neutropenia, elevated bilirubin, cardiac toxicity, unstable angina, myocardial infarction, persistent hypertension, peripheral sensory or motor neuropathy/pain, hepatic dysfunction (e.g., liver injury or liver disease, aspartate transaminase level elevation, alanine aminotransferase level elevation, etc.), reduced red and/or white blood cell count, hyperglycemia, nausea, decreased appetite, diarrhea, rash (e.g, maculopapular, acneiform, etc.) and hypersensitivity (e.g., increased sensitivity to bruise), photosensitivity, asthenia/fatigue, vomiting, stomatitis, oral mucositis, pancreatitis, dysgeusia, and dyspepsia after administration of said compound of formula (I) or a pharmaceutically acceptable salt thereof to said patient, and third reducing the administration of said compound of formula (I) or a pharmaceutically acceptable salt thereof to a daily dose of about 100 mg to about 450 mg via oral administration for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to a method of reducing at least one side effect selected from neutropenia, elevated bilirubin, cardiac toxicity, unstable angina, myocardial infarction, persistent hypertension, peripheral sensory or motor neuropathy/pain, hepatic dysfunction (e.g., liver injury or liver disease, aspartate transaminase level elevation, alanine aminotransferase level elevation, etc.), reduced red and/or white blood cell count, hyperglycemia, nausea, decreased appetite, diarrhea, rash (e.g, maculopapular, acneiform, etc.) and hypersensitivity (e.g., increased sensitivity to bruise), photosensitivity, asthenia/fatigue, vomiting, stomatitis, oral mucositis, pancreatitis, dysgeusia, and dyspepsia from prior treatment with the compound of formula (I) or a pharmaceutically acceptable salt thereof, comprising orally administering a therapeutically effective amount of the compound of formula (I) or a pharmaceutically acceptable salt thereof to the patient in a daily dose of about 100 mg to about 450 mg, preferably about 200 mg to about 400 mg or more preferably about 350 mg to about 400 mg, for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to the use of the compound of formula (I) or a pharmaceutically acceptable salt thereof for the manufacture of a medicament for treating or preventing a proliferative disease, wherein said medicament is orally administered to a patient in need thereof in a daily dose of about 100 mg to about 450 mg of said compound of formula (I) or a pharmaceutically acceptable salt thereof for at least two five-consecutive day cycles, wherein said medicament is not administered to the patient for a period of about 2 days to about 3 days between one five-consecutive day cycle and its subsequent five-consecutive day cycle.

In a further embodiment, the present invention relates to the use of the compound of formula (I) or a pharmaceutically acceptable salt thereof for treating or preventing a proliferative disease, wherein said compound of formula (I) or a pharmaceutically acceptable salt thereof is orally administered to a patient in need thereof in a daily dose of about 100 mg to about 450 mg for at least two five-consecutive day cycles, wherein said compound of formula (I) or a pharmaceutically acceptable salt thereof is not administered to the patient for a period of about 2 days to about 3 days between one five-consecutive day cycle and its subsequent five-consecutive day cycle.

In a further embodiment, the present invention relates to a pharmaceutical composition for use in the treatment or prevention of a proliferative disease in a patient in need thereof comprising an amount of about 100 mg to about 450 mg of a compound of formula (I) or pharmaceutically acceptable salt thereof together with one or more pharmaceutically acceptable excipients, wherein the pharmaceutical composition is orally administered to a patient for at least two five-consecutive day cycles and not administered to the patient for a period of about 2 days to about 3 days between one five-consecutive day cycle and its subsequent five-consecutive day cycle.

In a further embodiment, the present invention relates to a therapeutic regimen comprising orally administering a therapeutically effective amount of the compound of formula (I) or a pharmaceutically acceptable salt thereof to a patient in a daily dose of about 100 mg to about 450 mg for at least two five-consecutive day cycles, wherein said compound of formula (I) or a pharmaceutically acceptable salt thereof is not administered to the patient for a period of about 2 days to about 3 days between one five-consecutive day cycle and its subsequent five-consecutive day cycle.

In a further embodiment, the present invention relates to a package comprising a pharmaceutical composition comprising a compound of formula (I) or a pharmaceutically acceptable salt thereof in a daily dose of about 100 mg to about 450 mg together with one or more pharmaceutically acceptable excipients in combination with instructions to orally administer said pharmaceutical composition for at least two five-consecutive day cycles and to not administered said composition for a period of about 2 days to about 3 days between one five-consecutive day cycle and its subsequent five-consecutive day cycle.

DETAILED DESCRIPTION OF THE FIGURES

FIG. 1 shows concentration-time profiles after oral administration of Compound A at 12.5, 25 and 50 mg/kg qd in nude mice (FIG. 1A) and at 12.5, 25, 40 and 80 mg/kg qd in nude rats (FIG. 1B).

FIG. 2 shows observed versus predicted plasma concentrations after oral administration of Compound A at 50 mg/kg qd in nude mice (FIG. 2A) and 40 mg/kg qd in nude rats (FIG. 2B).

FIG. 3 shows observed versus predicted plasma concentrations after oral administration of Compound A at 6.25, 12.5, 25 and 50 mg/kg qd in nude mice (FIG. 3A) and at 6.25, 12.5, 25, 40, 50 and 80 mg/kg qd in nude rats (FIG. 3B) on continuous daily schedule.

FIG. 4A and FIG. 4B show observed versus predicted plasma concentrations after oral administration of Compound A at 40 mg/kg 2 qd on continuous daily schedule in nude mice in the PK modeling study (FIG. 4A) and the later repeat confirmatory PK modeling study (FIG. 4B).

FIG. 9 shows the relationship between plasma Compound A concentrations and plasma insulin levels (FIG. 9A) or blood glucose levels (FIG. 9B) measured in the same probe following Compound A treatment in nude mice.

FIG. 10 shows the relationship between plasma Compound A concentrations and plasma insulin levels (FIG. 10A) or blood glucose levels (FIG. 10B) measured in the same probe following Compound A treatment in nude rats.

FIG. 14 shows a simulated efficacy in Rat1-myr P110a tumor bearing nude rats treated orally with Compound A at 20 mg/kg in ALTERNATIVE SCHEDULE 1 (FIG. 14A) or 14 mg/kg qd on continuous daily schedule (FIG. 14B).

DETAILED DESCRIPTION OF THE INVENTION

Figure 5:
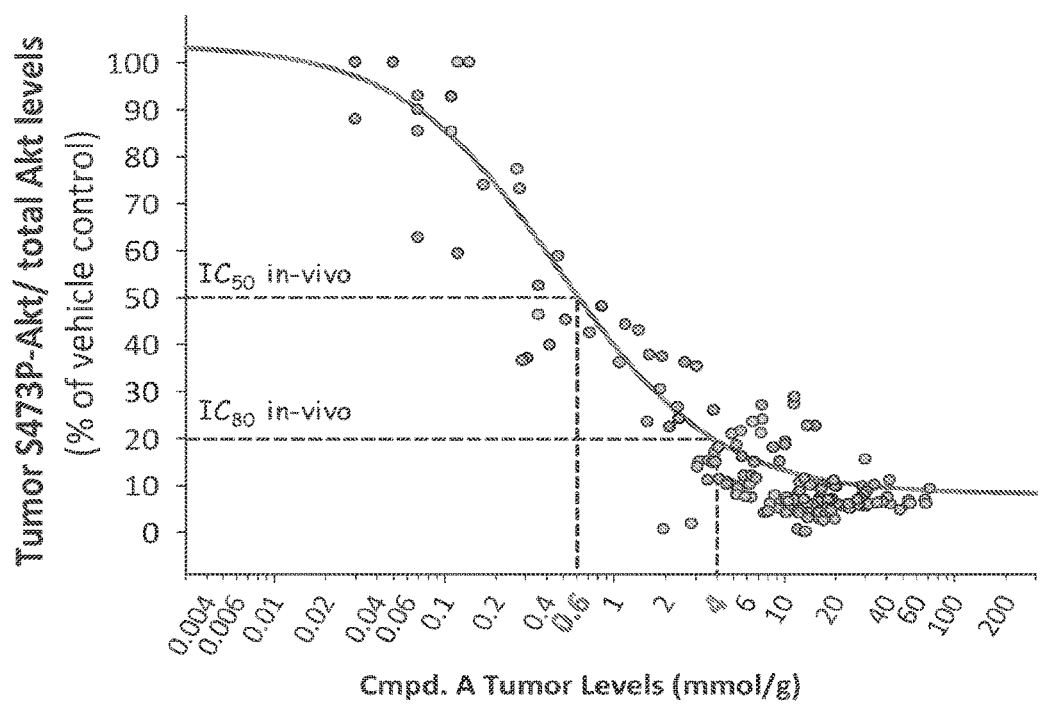
FIG. 5 shows the relationship between tumor tissue concentration and percent S473P-Akt inhibition measured concomitantly in the Rat1-myr P110a tumors at different time points post-treatment with Compound A.

The present invention relates to a method of treating or preventing a proliferative disease in a patient in need thereof, comprising orally administering a therapeutically effective amount of the compound of formula (I), as defined herein, or a pharmaceutically acceptable salt thereof to the patient in a daily dose of about 100 mg to about 450 mg for at least two five-consecutive day cycles, wherein said compound or a pharmaceutically acceptable salt thereof is not administered to the patient for a period of about two (2) days to about three (3) days between one five-consecutive day cycle and its subsequent five-consecutive day cycle.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "a phosphatidylinositol 3-kinase inhibitor" or "PI3K inhibitor" is defined herein to refer to a compound which targets, decreases or inhibits activity of the phosphatidylinositol 3-kinase.

The term "pharmaceutically acceptable" is defined herein to refer to those compounds, materials, compositions and/or dosage forms, which are, within the scope of sound medical judgment, suitable for contact with the tissues a patient without excessive toxicity, irritation allergic response and other problem complications commensurate with a reasonable benefit/risk ratio.

The term "treat", "treating" or "treatment" as used herein comprises a treatment or therapeutic regimen relieving, reducing or alleviating at least one symptom in a patient or effecting a delay of progression of a proliferative disorder. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disorder) and/or reduce the risk of developing or worsening a disorder.

The term "prevent", "preventing" or "prevention" as used herein comprises the prevention of at least one symptom associated with or caused by the state, disease or disorder being prevented.

The terms "clinically effective" or "therapeutically effective" is an observable improvement over the baseline clinically observable signs and symptoms of the state, disease or disorder treated with the therapeutic agent.

The term "therapeutically effective amount" is an amount sufficient to provide an observable improvement over the baseline clinically observable signs and symptoms of the state, disease or disorder treated with the therapeutic agent.

The term "pharmaceutical composition" is defined herein to refer to a mixture or solution containing at least one therapeutic agent to be administered to a patient, in order to prevent or treat a particular disease or condition affecting the patient.

The phrase "five-consecutive day cycle" as used herein means the specified therapeutic agent is administered to the patient during each day for five-consecutive days and then not administered for a period of time before the same therapeutic agent is next administered to the patient. It is understood that the therapeutic agent may be administered each day in a single dosage unit or multiple dosage units and/or administered each day in a single dose (once per day, q.d.) or divided doses (more than once per day, e.g., twice per day, b.i.d.).

The phrase "continuous daily schedule" as used herein means the therapeutic agent is administered to the patient during each day for at least seven days or for an unspecified period of time or for as long as treatment is necessary. It is understood that the therapeutic agent may be administered each day in a single dosage unit or multiple dosage units and/or administered each day in a single dose (once per day, q.d.) or divided doses (more than once per day, e.g., twice per day, b.i.d.).

The term "day" as used herein refers to either one calendar day or one 24-hour period.

The term "combination" is used herein to refer to either a fixed combination in one dosage unit form, a non-fixed combination or a kit of parts for the combined administration where the compound of formula (I) or a pharmaceutically acceptable salt thereof, and at least one additional therapeutic agent may be administered simultaneously, independently at the same time or separately within time intervals that allow that the combination partners show a cooperative, e.g., synergistic, effect. The term "fixed combination" means that the therapeutic agents, e.g. the compound of formula (I) or a pharmaceutically acceptable salt thereof and at least one additional therapeutic agent, are both administered to a patient simultaneously in the form of a single entity or dosage unit. The term "non-fixed combination" or "kit of parts" means that the therapeutic agents, e.g. the compound of formula (I) or a pharmaceutically acceptable salt thereof and at least one additional therapeutic agent, are both administered to a patient as separate entities or dosage units either simultaneously, concurrently or sequentially with no specific time limits, wherein such administration provides therapeutically effective levels of the two therapeutic agents in the body of the patient. The latter also applies to cocktail therapy, e.g. the administration of three or more therapeutic agents.

The term "combined administration" as used herein is defined to encompass the administration of the selected therapeutic agents to a single patient, and are intended to include treatment regimens in which the agents are not necessarily administered by the same route of administration or at the same time.

The terms "patient", "subject" or "warm-blooded animal" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a brain tumor disease. Particularly preferred, the patient or warm-blooded animal is human.

The terms "about" or "approximately" usually mean within 10%, more preferably within 5%, of a given value or range.

WO2010/029082 describes specific 2-carboxamide cycloamino urea derivatives, which have been found to have highly selective inhibitory activity for the alpha-isoform of phosphatidylinositol 3-kinase (PI3K). The alpha-isoform selective PI3K inhibitor suitable for the present invention is a compound having the following formula (I):

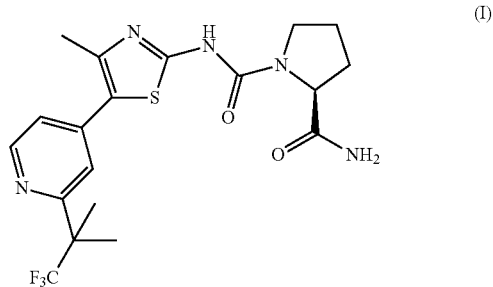 [SMILES: Cc1nc(NC(=O)N2CCC[C@H]2C(N)=O)sc1-c1ccnc(C(C)(C)C(F)(F)F)c1]

(hereinafter "compound of formula (I)" or "Compound A") or pharmaceutically acceptable salts thereof. The compound of formula (I) is also known as the chemical compound (S)-Pyrrolidine-1, 2-dicarboxylic acid 2-amide 1-({4-methyl-5-[2-(2,2,2-trifluoro-1,1-dimethyl-ethyl)-pyridin-4-yl]-thiazol-2-yl}-amide). The compound of formula (I), its pharmaceutically acceptable salts and suitable formulations are described in PCT Application No. WO2010/029082, which is hereby incorporated by reference in its entirety, and methods of its preparation have been described, for example, in Example 15 therein.

As used herein, the term "salts" (including "or salts thereof" or "or a salt thereof"), can be present alone or in mixture with free compound of formula (I) and are preferably pharmaceutically acceptable salts. Such salts are formed, for example, as acid addition salts, preferably with organic or inorganic acids, from the compound of formula (I) with a basic nitrogen atom, especially the pharmaceutically acceptable salts. Suitable in-organic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compound are employed (where applicable in the form of pharmaceutical preparations), and these are therefore preferred. In view of the close relationship between the compound of formula (I) in free form and those in the form of its salts, any reference to the free compound hereinbefore and hereinafter is to be understood as referring also to the corresponding salts, as appropriate and expedient. The salts of compound of the formula (I) are preferably pharmaceutically acceptable salts; suitable counter-ions forming pharmaceutically acceptable salts are known in the field.

The compound of formula (I) has been previously demonstrated to potently and selectively inhibit the alpha-isoform of the PI3K, including for example, Examples A and C of PCT Application No. WO2010/029082. In contrast to prior known PI3K inhibitors, the compound of formula (I) inhibits the alpha-isoform of PI3K ($IC_{50}$ of 0.008 μmol/L) more potently than the beta-isoform ($IC_{50}$ of 1.212 μmol/L), delta-isoform ($IC_{50}$ of 0.077 μmol/L), and gamma-isoform ($IC_{50}$ of 1.097 μmol/L) in cellular assays and lacks inhibitory activity against the Vps34, mTOR, DNA-PK and ATR. Further, the compound of formula (I) shows inhibitory activity against the wildtype alpha-isoform of PI3K, E545K mutant alpha-isoform of PI3K, and H1047R mutant alpha-isoform of PI3K.

The compound of formula (I) or its pharmaceutically acceptable salts may be orally administered at a dosage of about 100 mg to about 450 mg per day to a human patient in need thereof. The term "daily dose" refers to the total dosage amount of the therapeutic agent administered to a specific patient in any single day. In further embodiments, the compound of formula (I) may be administered to patient at a daily dose of about 200 to about 400 mg per day, or about 240 mg to about 400 mg per day, or about 300 mg to about 400 mg per day, or about 350 mg to about 400 mg per day. In a preferred embodiment, the compound of formula (I) is administered to a human patient at a daily dose of about 350 mg to about 400 mg per day.

The daily dose may be administered to the patient in single dose (once per day, q.d.) or divided doses (more than once per day, e.g., twice per day, b.i.d.). In one embodiment, the daily dose is administered in a once per day (q.d.). In a further embodiment, the daily dose is administered twice per day (b.i.d.)

The daily dose may be administered to the patient in a single dosage unit or amounts of multiple dosage units to make up the daily dose.

In accordance with the dosage regimen of the present invention, the compound of formula (I) or a pharmaceutically acceptable salt thereof is orally administered to a patient in need thereof in a daily dose of about 100 mg to about 450 mg for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle. Preferably, the compound or a pharmaceutically acceptable salt thereof is not administered for about 2 days between one five-consecutive day cycle and its subsequent five-consecutive day cycle.

In one embodiment, the compound of formula (I) or a pharmaceutically acceptable salt thereof is orally administered to a patient in need thereof once per day (q.d.) at a daily dose of about 100 mg to about 450 mg, preferably about 350 mg to about 400 mg, for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the compound of formula (I) or a pharmaceutically acceptable salt thereof is orally administered to a patient in need thereof twice per day (b.i.d.) at a daily dose of about 100 mg to about 450 mg, preferably about 350 mg to about 400 mg, for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

It is understood that the dosage regimen of the present invention may be alternatively defined relative to timing of the actual administrations of the compound of formula (I) or its pharmaceutically acceptable salt.

In one embodiment, the compound of formula (I) or a pharmaceutically acceptable salt thereof is orally administered to a patient in need thereof once per day (q.d.) at a daily dose of about 100 mg to about 450 mg, preferably about 350 mg to about 400 mg, for at least two five-consecutive day cycles, wherein said compound or a pharmaceutically acceptable salt thereof is not administered to the patient for a period of about 3 days between the last administration of said compound or a pharmaceutically acceptable salt thereof in one five-consecutive day cycle and the first administration of said compound or a pharmaceutically acceptable salt thereof in its subsequent five-consecutive day cycle.

In a further embodiment, the compound of formula (I) or a pharmaceutically acceptable salt thereof is orally administered to a patient in need thereof twice per day (b.i.d.) at a daily dose of about 100 mg to about 450 mg, preferably about 350 mg to about 400 mg, for at least two five-consecutive day cycles, wherein said compound or a pharmaceutically acceptable salt thereof is not administered for a period of about 2.5 days between the last administration of said compound or a pharmaceutically acceptable salt thereof in one five-consecutive day cycle and the first administration of said compound or a pharmaceutically acceptable salt thereof in its subsequent five-consecutive day cycle.

Proliferative diseases that may be treated or prevented by the administration of the compound of formula (I) or a pharmaceutically acceptable in accordance with the dosage regimen of the present invention are particularly those mediated by the alpha-isoform of the PI3K. It is understood that one embodiment of the present invention includes the treatment of the proliferative disease and that a further embodiment of the present invention includes the prevention of the proliferative disease.

Examples of proliferative diseases which may be treated or prevented in accordance with the present invention include, cancer, polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

Preferably, the proliferative disease is a cancer. The term "cancer" refers to tumors and/or cancerous cell growth preferably mediated by the alpha-isoform of the PI3K. In particular, the compounds are useful in the treatment of cancers including, for example, sarcoma, lung, bronchus, prostate, breast (including sporadic breast cancers and sufferers of Cowden disease), pancreas, gastrointestine, colon, rectum, colon carcinoma, colorectal adenoma, thyroid, liver, intrahepatic bile duct, hepatocellular, adrenal gland, stomach, gastric, glioma, glioblastoma, endometrial, melanoma, kidney, renal pelvis, urinary bladder, uterine corpus, uterine cervix, vagina, ovary, multiple myeloma, esophagus, a leukemia, acute myelogenous leukemia, chronic myelogenous leukemia, lymphocytic leukemia, myeloid leukemia, brain, oral cavity and pharynx, larynx, small intestine, non-Hodgkin lymphoma, melanoma, villous colon adenoma, a neoplasia, a neoplasia of epithelial character, lymphomas, a mammary carcinoma, basal cell carcinoma, squamous cell carcinoma, actinic keratosis, head and neck, polycythemia vera, essential thrombocythemia, myelofibrosis with myeloid metaplasia, and Waldenstroem disease.

Proliferative diseases mediated by the alpha-subunit of PI3K may include those showing overexpression or amplification of PI3K alpha, somatic mutation of PIK3CA or germline mutations or somatic mutation of PTEN or mutations and translocation of p85a that serve to up-regulate the p85-p110 complex. In a preferred embodiment, the cancer is a tumor and/or cancerous growth mediated by the alpha isoform of PI3K.

In one embodiment, the proliferative disease is a cancer selected from a cancer of the lung, bronchus, prostate, breast (including sporadic breast cancers and sufferers of Cowden disease), colon, rectum, colon carcinoma, colorectal adenoma, pancreas, gastrointestine, hepatocellular, stomach, gastric, ovary, squamous cell carcinoma, and head and neck.

In a further embodiment, the proliferative disease is a cancer selected from a cancer of the breast, colon, rectum, colon carcinoma, colorectal adenoma, endometrial, and cervical.

In a further embodiment, the proliferative disease is a cancer selected from a cancer of the lung, breast (including sporadic breast cancers and sufferers of Cowden disease), gastric, ovary and head and neck.

In a further embodiment, the present invention relates to the treatment of a cancer by the administration of the compound of formula (I) or a pharmaceutically acceptable in accordance with the dosage regimen of the present invention.

It is believed that reducing the dosing of this potent alpha-isoform selective PI3K inhibitor compound of formula (I) or a pharmaceutically acceptable salt thereof from oral administration at (a) a daily dose of about 100 mg to about 450 mg daily on a continuous daily schedule to (b) a daily dose of about 100 mg to about 450 mg for at least two five-consecutive day cycles, wherein said compound is not administered for a period of about 2 days to about 3 days between said five-consecutive day cycles, is effective to treat or prevent a proliferative disease while relieving, reducing, or alleviating the severity, occurrence rate and/or frequency of any side effects. This is particularly applicable to treatment or prevention of a cancer.

Examples of such side effects which may relieved, reduced, or alleviated by the dosage regimen of the present invention include, but are not limited to, neutropenia, elevated bilirubin, cardiac toxicity, unstable angina, myocardial infarction, persistent hypertension, peripheral sensory or motor neuropathy/pain, hepatic dysfunction (e.g., liver injury or liver disease, aspartate transaminase level elevation, alanine aminotransferase level elevation, etc.), reduced red and/or white blood cell count, hyperglycemia, nausea, decreased appetite, diarrhea, rash (e.g, maculopapular, acneiform, etc.) and hypersensitivity (e.g., increased sensitivity to bruise), photosensitivity, asthenia/fatigue, vomiting, stomatitis, oral mucositis, pancreatitis, dysgeusia, and dyspepsia. It is understood by one of ordinary skill in the art how to assess such side effects in a patient suffering from proliferative diseases using one's experience or prior knowledge and/or by referencing standard side effect grading criteria, for example, by assessing such patient using the NCI Common Terminology Criteria for Adverse Events, version 4.03 (website located at: http://evs.nci.nih.gov/ftp1/CTCAE/About.html), which is hereby incorporated by reference in its entirety.

In a preferred embodiment, the side effect relieved, reduced, or alleviated by the dosage regimen of the present invention is a condition selected from hyperglycemia, nausea, decreased appetite, diarrhea, rash (e.g, maculopapular, acneiform, etc.) and hypersensitivity (e.g., increased sensitivity to bruise), photosensitivity, asthenia/fatigue, vomiting, stomatitis, oral mucositis, dysgeusia, and dyspepsia. More preferably, the side effect relieved, reduced, or alleviated by the dosage regimen of the present invention is hyperglycemia.

It can be shown by established test models that the dosage regimen of the present invention results in the beneficial effects described herein before. The person skilled in the art is fully enabled to select a relevant test model to prove such beneficial effects. The pharmacological activity of the compound of formula (I) or its pharmaceutically acceptable salt may, for example, be demonstrated in a clinical study, an animal study or in a test procedure as essentially described hereinafter.

Suitable clinical studies are in particular, for example, open label, dose escalation studies in patients with a proliferative disease, including for example a tumor disease, e.g., breast cancer, wherein said patients are orally administered the compound of formula (I) in accordance with the dosage regimen of the present invention. Preferably, patients are assigned to different groups wherein at least one group is administered the compound of formula (I) on a continuous daily schedule and at least one group is administered the compound of formula (I) in accordance with the dosage regimen of the present invention. Such studies prove in particular the efficacy of the therapeutic agent and its impact on existing or potential side effects. The beneficial effects on a proliferative disease may be determined directly through the results of these studies which are known as such to a person skilled in the art. Such studies may be, in particular, suitable to compare the effects of a continuous daily schedule using the therapeutic agents and the dosing schedule of the present invention. Each patient may receive doses of the compound of formula (I) or its pharmaceutically acceptable salt either once per day or more than once (e.g., twice) per day. The efficacy of the treatment may be determined in such studies, e.g., after 12, 18 or 24 weeks by evaluation of symptom scores and/or tumor size measurements every 6 weeks.

In accordance with the present invention, the compound of formula (I) or a pharmaceutically acceptable salt thereof is preferably used or administered in the form of pharmaceutically compositions that contain a therapeutically effective amount of the compound of formula (I) or pharmaceutically acceptable salt thereof together with one or more pharmaceutically acceptable excipients suitable for oral administration. The pharmaceutical composition may comprise an amount of about 100 mg to about 450 mg of a compound of formula (I) or pharmaceutically acceptable salt thereof to be administered in a single dosage unit. Alternatively, the pharmaceutical composition may comprise an amount of the compound of formula (I) or pharmaceutically acceptable salt thereof which is subdivided into multiple dosage units and administered for a daily dosage of about 100 mg to about 450 mg of the compound of formula (I) or pharmaceutically acceptable salt thereof.

The pharmaceutical compositions used according to the present invention can be prepared in a manner known per se to be suitable for oral administration to mammals (warm-blooded animals), including humans. Pharmaceutical compositions for oral administration may include, for example, those in dosage unit forms, such as sugar-coated tablets, tablets, capsules, sachets and furthermore ampoules. If not indicated otherwise, these are prepared in a manner known per se, for example by means of conventional mixing, granulating, sugar-coating, dissolving or lyophilizing processes. It will be appreciated that the amount of the active ingredient contained in an individual dose or dosage unit need not in itself constitute a therapeutically effective amount since the necessary effective amount can be reached by administration of a plurality of dosage units.

The novel pharmaceutical composition may contain, for example, from about 10% to about 100%, preferably from about 20% to about 60%, of the active ingredient.

In preparing the compositions for oral dosage unit form, any of the usual pharmaceutically acceptable excipients may be employed, such as, for example, water, glycols, oils, alcohols, flavoring agents, preservatives, coloring agents; or excipients such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed.

One of ordinary skill in the art may select one or more of the aforementioned excipients with respect to the particular desired properties of the dosage unit form by routine experimentation and without any undue burden. The amount of each excipient used may vary within ranges conventional in the art. The following references which are all hereby incorporated by reference disclose techniques and excipients used to formulate oral dosage forms. (See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2003).)

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

A dosage unit form containing the compound of formula (I) or a pharmaceutically acceptable salt thereof may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose, Sodium stearyl fumarate and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

In one embodiment, the present invention relates to a pharmaceutical composition for use in the treatment or prevention of a proliferative disease in a patient in need thereof comprising an amount of about 100 mg to about 450 mg of a compound of formula (I) or pharmaceutically acceptable salt thereof together with one or more pharmaceutically acceptable excipients, wherein the pharmaceutical composition is orally administered to a patient for at least two five-consecutive day cycles and not administered to the patient for a period of about 2 days to about 3 days between one five-consecutive day cycle and its subsequent five-consecutive day cycle.

In one embodiment, the present invention relates to a method of treating or preventing a proliferative disease in a patient in need thereof, comprising orally administering a therapeutically effective amount of the compound of formula (I) or a pharmaceutically acceptable salt thereof to the patient in a daily dose of about 100 mg to about 450 mg, preferably about 200 mg to about 400 mg or more preferably about 350 mg to about 400 mg, for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle. Preferably, the compound or a pharmaceutically acceptable salt thereof is not administered for about 2 days between one five-consecutive day cycle and its subsequent five-consecutive day cycle.

In a further embodiment, the present invention relates to a method of treating or preventing a proliferative disease in a patient in need thereof, comprising orally administering a therapeutically effective amount of the compound of formula (I) or a pharmaceutically acceptable salt thereof to the patient once per day (q.d.) at a daily dose of about 100 mg to about 450 mg for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to a method of treating or preventing a proliferative disease in a patient in need thereof, comprising orally administering a therapeutically effective amount of the compound of formula (I) or a pharmaceutically acceptable salt thereof to the patient twice per day (b.i.d.) at a daily dose of about 100 mg to about 450 mg for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to a method of treating or preventing a proliferative disease in a patient in need thereof, comprising orally administering a therapeutically effective amount of the compound of formula (I) or a pharmaceutically acceptable salt thereof to the patient once per day (q.d.) at a daily dose of about 100 mg to about 450 mg for at least two five-consecutive day cycles, wherein said compound or a pharmaceutically acceptable salt thereof is not administered to the patient for a period of about 3 days between the last administration of said compound or a pharmaceutically acceptable salt thereof in one five-consecutive day cycle and the first administration of said compound or a pharmaceutically acceptable salt thereof in its subsequent five-consecutive day cycle.

In a further embodiment, the present invention relates to a method of treating or preventing a proliferative disease in a patient in need thereof, comprising orally administering a therapeutically effective amount of the compound of formula (I) or a pharmaceutically acceptable salt thereof to the patient twice per day (b.i.d.) at a daily dose of about 100 mg to about 450 mg, preferably about 350 mg to about 400 mg, for at least two five-consecutive day cycles, wherein said compound or a pharmaceutically acceptable salt thereof is not administered for a period of about 2.5 days between the last administration of said compound or a pharmaceutically acceptable salt thereof in one five-consecutive day cycle and the first administration of said compound or a pharmaceutically acceptable salt thereof in its subsequent five-consecutive day cycle.

In a further embodiment, the present invention relates to a method of treating or preventing a proliferative disease in accordance with the dosage regimen herein, wherein the compound of formula (I) or its pharmaceutically acceptable salt thereof is administered in two or more of said five-consecutive day cycles until the relief, reduction, or alleviation of the severity, occurrence rate, or frequency of at least one side effect in said patient.

In a further embodiment, the present invention relates to a method of treating or preventing a proliferative disease in accordance with the dosage regimen herein, wherein the compound of formula (I) or its pharmaceutically acceptable salt thereof is administered in two or more of said five-consecutive day cycle until the progression of the disease.

In a further embodiment, the present invention relates to a method of treating or preventing a proliferative disease comprising first administering to a patient in need thereof a compound of formula (I) or a pharmaceutically acceptable salt thereof in amount of about 100 mg to about 450 mg daily on a continuous daily schedule via oral administration, second determining said patient has a side effect selected from neutropenia, elevated bilirubin, cardiac toxicity, unstable angina, myocardial infarction, persistent hypertension, peripheral sensory or motor neuropathy/pain, hepatic dysfunction (e.g., liver injury or liver disease, aspartate transaminase level elevation, alanine aminotransferase level elevation, etc.), reduced red and/or white blood cell count, hyperglycemia, nausea, decreased appetite, diarrhea, rash (e.g, maculopapular, acneiform, etc.) and hypersensitivity (e.g., increased sensitivity to bruise), photosensitivity, asthenia/fatigue, vomiting, stomatitis, oral mucositis, pancreatitis, dysgeusia, and dyspepsia after administration of said compound of formula (I) or a pharmaceutically acceptable salt thereof to said patient, and third reducing the administration of said compound of formula (I) or a pharmaceutically acceptable salt thereof to a daily dose of about 100 mg to about 450 mg via oral administration for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to a method of reducing at least one side effect selected from neutropenia, elevated bilirubin, cardiac toxicity, unstable angina, myocardial infarction, persistent hypertension, peripheral sensory or motor neuropathy/pain, hepatic dysfunction (e.g., liver injury or liver disease, aspartate transaminase level elevation, alanine aminotransferase level elevation, etc.), reduced red and/or white blood cell count, hyperglycemia, nausea, decreased appetite, diarrhea, rash (e.g, maculopapular, acneiform, etc.) and hypersensitivity (e.g., increased sensitivity to bruise), photosensitivity, asthenia/fatigue, vomiting, stomatitis, oral mucositis, pancreatitis, dysgeusia, and dyspepsia from prior treatment with the compound of formula (I) or a pharmaceutically acceptable salt thereof, comprising orally administering a therapeutically effective amount of the compound of formula (I) or a pharmaceutically acceptable salt thereof to the patient in a daily dose of about 100 mg to about 450 mg, preferably about 200 mg to about 400 mg or more preferably about 350 mg to about 400 mg, for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

Further, the present invention includes a method of treating or preventing a proliferative disorder in accordance with any other embodiment disclosed above for the present invention.

In one embodiment, the present invention relates to the use of the compound of formula (I) or a pharmaceutically acceptable salt thereof for the manufacture of a medicament for treating or preventing a proliferative disease, wherein said medicament is orally administered to a patient in need thereof in a daily dose of about 100 mg to about 450 mg, preferably about 200 mg to about 400 mg or more preferably about 350 mg to about 400 mg, of said compound of formula (I) or a pharmaceutically acceptable salt thereof for at least two five-consecutive day cycles, wherein said medicament is not administered to the patient for a period of about 2 days to about 3 days between one five-consecutive day cycle and its subsequent five-consecutive day cycle.

In a further embodiment, the present invention relates to the use of the compound of formula (I) or a pharmaceutically acceptable salt thereof for the manufacture of a medicament for treating or preventing a proliferative disease, wherein said medicament is orally administered to a patient in need thereof once per day (q.d.) in a daily dose of about 100 mg to about 450 mg for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to the use of the compound of formula (I) or a pharmaceutically acceptable salt thereof for the manufacture of a medicament for treating or preventing a proliferative disease, wherein said medicament is orally administered to a patient in need thereof twice per day (b.i.d.) in a daily dose of about 100 mg to about 450 mg for at least two five-consecutive day cycles, wherein said compound or a pharmaceutically acceptable salt thereof is not administered to the patient for a period of about 2 days to about 3 days between one five-consecutive day cycle and its subsequent five-consecutive day cycle.

In a further embodiment, the present invention relates to the use of the compound of formula (I) or a pharmaceutically acceptable salt thereof for the manufacture of a medicament for treating or preventing a proliferative disease, wherein said medicament is orally administered to a patient in need thereof once per day (q.d.) in a daily dose of about 100 mg to about 450 mg for at least two five-consecutive day cycles, wherein said compound or a pharmaceutically acceptable salt thereof is not administered to the patient for a period of about 3 days between the last administration of said compound or a pharmaceutically acceptable salt thereof in one five-consecutive day cycle and the first administration of said compound or a pharmaceutically acceptable salt thereof in its subsequent five-consecutive day cycle.

In a further embodiment, the present invention relates to the use of the compound of formula (I) or a pharmaceutically acceptable salt thereof for the manufacture of a medicament for treating or preventing a proliferative disease, wherein said medicament is orally administered to a patient in need thereof twice per day (b.i.d.) in a daily dose of about 100 mg to about 450 mg for at least two five-consecutive day cycles, wherein said compound or a pharmaceutically acceptable salt thereof is not administered for a period of about 2.5 days between the last administration of said compound or a pharmaceutically acceptable salt thereof in one five-consecutive day cycle and the first administration of said compound or a pharmaceutically acceptable salt thereof in its subsequent five-consecutive day cycle.

In a further embodiment, the present invention relates to the use of the compound of formula (I) or a pharmaceutically acceptable salt thereof for the manufacture of a medicament for treating or preventing a proliferative disease, wherein said medicament is orally administered in accordance with the dosage regimen herein, wherein the compound of formula (I) or its pharmaceutically acceptable salt thereof is administered in two or more of said five-consecutive day cycles until the relief, reduction, or alleviation of the severity, occurrence rate, or frequency of at least one side effect in said patient.

In a further embodiment, the present invention relates to the use of the compound of formula (I) or a pharmaceutically acceptable salt thereof for the manufacture of a medicament for treating or preventing a proliferative disease, wherein said medicament is orally administered in accordance with the dosage regimen herein, wherein the compound of formula (I) or its pharmaceutically acceptable salt thereof is administered in two or more of said five-consecutive day cycles until the progression of the disease.

In a further embodiment, the present invention relates to the use of the compound of formula (I) or a pharmaceutically acceptable salt thereof for the manufacture of a medicament for treating or preventing a proliferative disease, wherein said medicament is first orally administered in amount of about 100 mg to about 450 mg daily dose on a continuous daily schedule and subsequently reduced to an administered amount of about 100 mg to about 450 mg daily dose for at least two five-consecutive day cycles via oral administration, wherein said compound or a pharmaceutically acceptable salt thereof is not administered to the patient for a period of about 2 days to about 3 days between one five-consecutive day cycle and its subsequent five-consecutive day cycle.

Further, the present invention includes any use of the compound of formula (I) or a pharmaceutically acceptable salt thereof for the manufacture of a medicament for treating or preventing a proliferative disease in accordance with the methods of treatment or any embodiment disclosed above for the present invention.

In one embodiment, the present invention relates to the use of the compound of formula (I) or a pharmaceutically acceptable salt thereof for treating or preventing a proliferative disease, wherein said compound of formula (I) or a pharmaceutically acceptable salt thereof is orally administered to a patient in need thereof in a daily dose of about 100 mg to about 450 mg for at least two five-consecutive day cycles, wherein said compound of formula (I) or a pharmaceutically acceptable salt thereof is not administered to the patient for a period of about 2 days to about 3 days between one five-consecutive day cycle and its subsequent five-consecutive day cycle.

Further, the present invention includes any use of the compound of formula (I) or a pharmaceutically acceptable salt thereof in accordance with the methods of treatment, uses for the manufacture of a medicament, or any embodiment disclosed above for the present invention.

The present invention further relates to a therapeutic regimen comprising orally administering a therapeutically effective amount of the compound of formula (I) or a pharmaceutically acceptable salt thereof to a patient in need thereof in a daily dose of about 100 mg to about 450 mg for at least two five-consecutive day cycles, wherein said compound of formula (I) or a pharmaceutically acceptable salt thereof is not administered to the patient for a period of about 2 days to about 3 days between one five-consecutive day cycle and its subsequent five-consecutive day cycle.

The present invention further relates to the compound of formula (I) or a pharmaceutically acceptable salt thereof administered in combination with at least one additional therapeutic agent for the treatment or prevention of a proliferative disease, wherein the compound of formula (I) or a pharmaceutically acceptable salt thereof is administered in a daily dose of about 100 mg to about 450 mg for at least two five-consecutive day cycles, wherein said compound of formula (I) or a pharmaceutically acceptable salt thereof is not administered to the patient for a period of about 2 days to about 3 days between one five-consecutive day cycle and its subsequent five-consecutive day cycle.

Suitable therapeutic agents for use in accordance with the present invention include, but are not limited to, kinase inhibitors, anti-estrogens, anti androgens, other inhibitors, cancer chemotherapeutic drugs, alkylating agents, chelating agents, biological response modifiers, cancer vaccines, agents for antisense therapy. Examples are set forth below:

A. Kinase Inhibitors including inhibitors of Epidermal Growth Factor Receptor (EGFR) kinases such as small molecule quinazolines, for example gefitinib (U.S. Pat. Nos. 5,457,105, 5,616,582, and 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552), and cetuximab; Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. Nos. 6,605,617 and 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VM DA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, MEK162, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens: Estrogen-targeting agents include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens: Androgen-targeting agents including flutamide, bicalutamide, finasteride, aminoglutethamide, ketoconazole, and corticosteroids.

D. Other Inhibitors including Protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; cyclooxygenase 2 (COX-2) inhibitors including non-steroidal antiinflammatory drugs I (NSAIDs); letrozole; exemestane; and eribulin.

E. Cancer Chemotherapeutic Drugs including anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents including VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); 06-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents including tetrathiomolybdate (WO 01/60814); RP-697; Chimeric T84.66 (cT84.66); gadofosveset (Vasovist®); deferoxamine; and bleomycin optionally in combination with electorporation (EPT).

H. Biological Response Modifiers, such as immune modulators, including staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexalen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines: Anticancer vaccines including Avicine® (Tetrahedron Lett. 26:2269-70 (1974)); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy: Anticancer agents including antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

In one embodiment, the additional therapeutic agent is selected from gefinitib, erlotinib, bevacizumab or Avastin®, pertuzumab, trastuzumab, MEK162, tamoxifen, fulvestrant, capecitabine, cisplatin, carboplatin, cetuximab, paclitaxel, temozolamide, letrozole, or exemestane.

The structure of the drug substances identified by code numbers, generic or trade names may be taken from the Internet, actual edition of the standard compendium "The Merck Index" or from databases, e.g., Patents International, e.g., IMS World Publications, or the publications mentioned above and below. The corresponding content thereof is hereby incorporated by reference.

The compound of formula (I) and the additional therapeutic agent may be administered together in a single pharmaceutical composition, separately in two or more separate unit dosage forms, or sequentially. The pharmaceutical composition or dosage unit form comprising the additional therapeutic agent may be prepared in a manner known per se and are those suitable for enteral, such as oral or rectal, topical, and parenteral administration to subjects, including mammals (warm-blooded animals) such as humans.

In particular, a therapeutically effective amount of each of the therapeutic agents may be administered simultaneously or sequentially and in any order, and the components may be administered separately or as a fixed combination. For example, the combination of the present invention may comprise: (i) administration of the first therapeutic agent (a) in free or pharmaceutically acceptable salt form; and (ii) administration of an therapeutic agent (b) in free or pharmaceutically acceptable salt form, simultaneously or sequentially in any order, in jointly therapeutically effective amounts, preferably in synergistically effective amounts, e.g., in daily or intermittent dosages corresponding to the amounts described herein. The individual therapeutic agents of the combination may be administered separately at different times during the course of therapy or concurrently in divided or single combination forms.

"Synergy" or "synergistic" refers to the action of two therapeutic agents such as, for example, (a) a compound of formula (I) or a pharmaceutically acceptable salt thereof and (b) an aromatase inhibitor, producing an effect, for example, slowing the symptomatic progression of a cancer disease or disorder, particularly cancer, or symptoms thereof, which is greater than the simple addition of the effects of each therapeutic agent administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the therapeutic agent combination. The corresponding graphs associated with the equations referred to above are the concentration-effect curve, isobologram curve and combination index curve, respectively. Synergy may be further shown by calculating the synergy score of the combination according to methods known by one of ordinary skill.

The effective dosage of each of therapeutic agent (a) or therapeutic agent (b) employed in the combination may vary depending on the particular compound or pharmaceutical composition employed, the mode of administration, the condition being treated, the severity of the condition being treated. Thus, the dosage regimen of the combination is selected in accordance with a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the therapeutic agent required to prevent, counter or arrest the progress of the condition. Optimal precision in achieving concentration of therapeutic agent within the range that yields efficacy requires a regimen based on the kinetics of the therapeutic agent's availability to target sites. This involves a consideration of the distribution, equilibrium, and elimination of a therapeutic agent.

Examples of proliferative diseases that may be treated with a combination of a compound of formula (I) or a pharmaceutically acceptable salt thereof and at least one additional therapeutic agent include, but not limited to, those set forth above.

It can be shown by established test models that the combination of the present invention results in the beneficial effects described herein before. The person skilled in the art is fully enabled to select a relevant test model to prove such beneficial effects. The pharmacological activity of a combination of the present invention may, for example, be demonstrated in a clinical study or in a test procedure as essentially described hereinafter.

Suitable clinical studies are in particular, for example, open label, dose escalation studies in patients with a proliferative disease, including for example a tumor disease, e.g., breast cancer. Such studies prove in particular the synergism of the therapeutic agents of the combination of the present invention. The beneficial effects on a proliferative disease may be determined directly through the results of these studies which are known as such to a person skilled in the art. Such studies may be, in particular, suitable to compare the effects of a monotherapy using the therapeutic agents and a combination of the present invention. In one embodiment, the dose of the alpha-isoform selective PI3K inhibitor compound of formula (I) or its pharmaceutically acceptable salt is escalated until the Maximum Tolerated Dosage is reached, and the combination partner is administered with a fixed dose. Alternatively, the compound of formula (I) or its pharmaceutically acceptable salt may be administered in a fixed dose and the dose of the combination partner may be escalated. Each patient may receive doses of the compound of formula (I) or its pharmaceutically acceptable salt either once per day or more than once (e.g., twice) per day. The efficacy of the treatment may be determined in such studies, e.g., after 12, 18 or 24 weeks by evaluation of symptom scores every 6 weeks.

In the combination of the present invention, the compound of formula (I) or a pharmaceutically acceptable salt thereof is administered in a daily dose of about 100 mg to about 450 mg for at least two five-consecutive day cycles, wherein said compound of formula (I) or a pharmaceutically acceptable salt thereof is not administered to the patient for a period of about 2 days to about 3 days between one five-consecutive day cycle and its subsequent five-consecutive day cycle.

In one embodiment, the present invention relates to a method of treating a treating or preventing a proliferative disease by administration in accordance with the dosage regimen of the present invention, wherein said compound of formula (I) or a pharmaceutically acceptable salt thereof is administered in combination with at least one additional therapeutic agent.

In a further embodiment, the present invention relates to the use of the compound of formula (I) or a pharmaceutically acceptable salt thereof for the manufacture of a medicament for treating or preventing a proliferative disease in accordance with the dosage regimen of the present invention, wherein said compound of formula (I) or a pharmaceutically acceptable salt thereof is administered in combination with at least one additional therapeutic agent.

In a further embodiment, the present invention relates to the use of the compound of formula (I) or a pharmaceutically acceptable salt thereof for treating or preventing a proliferative disease in accordance with the dosage regimen of the present invention, wherein said compound of formula (I) or a pharmaceutically acceptable salt thereof is administered in combination with at least one additional therapeutic agent.

The present invention further relates to a package comprising a pharmaceutical composition comprising a compound of formula (I) or a pharmaceutically acceptable salt thereof in a daily dose of about 100 mg to about 450 mg together with one or more pharmaceutically acceptable excipients in combination with instructions to orally administer said pharmaceutical composition for at least two five-consecutive day cycles and to not administered said composition for a period of about 2 days to about 3 days between one five-consecutive day cycle and its subsequent five-consecutive day cycle.

Utility of the dosage regimen of the compounds of formula (I) of the present invention may be demonstrated in vitro, in animal test methods as well as in clinic studies. For example in the utility of the compounds of formula (I) in accordance with the present invention may be demonstrated in accordance with the methods hereinafter described:

Example 1

Materials and Methods

Animals and Maintenance Conditions:

Experiments were performed in female Hsd: Athymic Nude-nu CPB mice (Harlan Winkelmann, Germany). Animals were between 12 and 14 weeks of age at treatment start and housed under Optimized Hygienic Conditions (OHC) in Makrolon type III cages (max. 5 animals per cage) with free access to food and water. In addition, experiments were also performed in female nude Rowett rats Hsd: RH-Fox1mu (Harlan (The Netherlands). Animals were 6-9 weeks of age at time of application of the compound. Animals were housed under Optimized Hygienic Conditions in Makrolon type III cages (max. 2 animals per cage) with free access to food and water. They were allowed to adapt for at least 6 days before the experiment was started.

Cell Line and Cell Culture:

Rat1-Myr-p110α cells were grown in Dulbecco's Modified Eagle Medium (DMEM) culture medium containing 4.5 g/l glucose supplemented with 10% heat-inactivated fetal calf serum (FCS), 2 mM L-glutamine, 1 mM sodium pyruvate and incubated at 37° C. in a 5% $CO_2$ humidified atmosphere. Cells were harvested with trypsin-EDTA, resuspended in culture medium (with additives) and counted with a Casy® system. Finally, cells are centrifuged, suspended in ice-cold Hanks' balanced salt solution (HBSS) at a concentration of $3\times10^7$ cells/ml. Cell culture reagents were purchased from BioConcept (Allschwil, Switzerland).

Rat1-myr-p110α cells were generated by the method described in Maira et al., Molecular Cancer Therapeutics, 11:317-328 (2012), which is incorporated herein by reference in its entirety. Briefly, Rat1 cells were transfected to stably express the constitutively active form of the catalytic PI3K class I p110 isoforms a by addition of a myristylation signal to the N-terminus.

Establishment of Tumor Xenografts In Vivo:

Rat1-Myr-p110α tumors were established by subcutaneous injection of $5\times10^6$ cells in 100 µL HBSS (Sigma #H8264) into the right flank of nude mice or nude rats. For the efficacy experiments, treatments were initiated when the mean tumor volumes were approx. 300 $mm^3$ (14 to 15 days post tumor cells injection). For single dose PK/PD experiments, animals were treated once orally with Compound A when the tumors reached a size of approx. 400-500 $mm^3$ (21 to 23 days post tumor cells injection).

Compound Formulation and Animal Treatment:

Compound A was prepared for dosing as homogenous suspensions in 1% carboxymethyl cellulose: 0.5% Tween® 80: 98.5% deionized water. Fresh suspensions were prepared once every 4 days and stored at 4° C. Compound A or vehicle was administered orally at a volume of 10 mL/kg.

Evaluation of Antitumor Activity:

Tumor volumes were measured with calipers and determined according to the formula: length×$diameter^2$×π/6. In addition to presenting changes of tumor volumes over the course of treatments, antitumor activity is expressed as T/C % (mean change of tumor volume of treated animals/mean change of tumor volume of control animals)×100. Regressions (%) were calculated according to the formula ((mean tumor volume at end of treatment−mean tumor volume at start of treatment)/mean tumor volume at start of treatment)×100. Body weights and tumor volumes were recorded two to three times a week.

Sampling:

Blood samples were collected at different time points post the last treatment (1 hour, 2 hour, 4 hour, 8 hour, 12 hour, 16 hour and 24 hour, n=2-3 per time point) into tubes coated with K-EDTA. Blood samples were centrifuged and collected plasma immediately frozen at −80° C. until final processing. Tumors were collected at sacrifice at 7 time points (1 hour, 2 hour, 4 hour, 8 hour, 12 hour, 16 hour and 24 hour, n=2-3 per time point), snap frozen and kept at −80° C. until final processing.

Pharmacokinetic/Pharmacodynamic Analyses

A. Animal Tissue Pulverization:

After dissection, the tumors were snap-frozen in liquid nitrogen and stored at −80° C. Frozen tumors were pulverized using a Retsch ball mixer mill MM20 (Arlesheim, Switzerland) with metal cylinders that were pre-cooled to −80° C. in a freezer. Powder was scrapped from metal cylinders on dry ice and transferred into pre-cooled 1.5 mL Eppendorf tubes while avoiding melting.

B. Bioanalytics (LC/MS-MS) for Quantification of Compound A:

Concentrations of Compound A in plasma and tumor were determined in a separate run by using ultra-high-pressure liquid chromatography/tandem mass spectrometry (UPLC/MS-MS). Following addition of 25 µL of internal standard (1 µg/mL) to analytical aliquots (25 µL) of plasma or (20 mg) tumor powder, the proteins were precipitated by the addition of 200 µL acetonitrile. The supernatant were transferred in a fresh vial. After evaporation to dryness the samples were re-dissolved in 60 µL acetonitrile/water (1/1 v/v). An aliquot (5 µL) of this solution was separated on a ACQUITY UPLC BEH C18 column (Waters™ 1.7 µm particle size, 2.1×50 mm) with a mobile phase consisting of a mixture of 0.1% formic acid in water (solvent A) and 0.1% formic acid in acetonitrile (solvent B). Gradient programming was used with a flow rate of 600 µL/min. After equilibration with 95% solvent A, 5 µL of sample was injected. Following a latency period of 0.25 min, the sample was eluted with a linear gradient of 5-100% solvent B over a period of 0.65 minutes followed by a 0.35 minutes hold. The column was prepared for the next sample by re-equilibrating over 0.25 minutes to the starting conditions. The column eluent was directly introduced into the ion source of the triple quadrupole mass spectrometer TQD™ (Waters Corporation, Milford, Mass., USA) controlled by Masslynx™ 4.1 software. Electrospray positive ionization (ESI+) multiple reaction monitoring was used for the MS/MS detection of the analyte. Precursor to product ion transitions for Compound A and the corresponding internal standard are summarized in the following Table:

| | Precursor ion [m/z] | Product ion [m/z] | Internal standard | Precursor ion [m/z] | Product ion [m/z] |
|---|---|---|---|---|---|
| Compound A | 442.10 | 328.10 | Compound B | 387.10 | 273.10 |

The limit of quantification (LOQ) for Compound A was set to 2.5 ng/mL (CV and overall bias less than 30%). Regression analysis and further calculations were performed using QuanLynx™ 4.1 (Micromass) and Excel™ 2007 (Microsoft). Concentrations of unknown samples were back-calculated based on the peak area ratios of analyte/IS from a calibration curve constructed using calibration samples spiked in blank plasma or tumor obtained from animals treated with vehicle.

C. Quantification of Ser473 P-Akt and Akt Via Reverse Phase Protein Array (RPPA) Approach.

Approximately 20 mg of frozen tissue powder was weighed out and lyzed in 100 µL NP40 protein lysis buffer mix (Lysis buffer stock (4° C.): 2.5 mL Tris HCL 2M pH 7.8 RT, 1 mL NP40 (100%) RT, 2.4 mL NaCl 5M RT, 2.5 mL NaF 1M RT, 4 mL 1M beta glycerol phosphate disodium salt penthahydrate −20° C., and water till 100 mL; Lysis buffer solution (4° C.): 10 mL lysis buffer stock; 10 uL Na3VO3 100 mM 4° C., 10 uL DTT 1M −20° C., 10 uL PMSF 100 mM 4° C., 10 uL Benzamidine 1M −20° C., and 10 uL Microcystin −20° C.).

Each sample was vortexed and centrifuged for 10 minutes at 10,000 rpm. A freezing thawing cycle was performed at −80° C. for 30 minutes. The samples were stored, after an additional centrifugation step at 10 000 rpm for 10 minutes, at −80° C. for further analysis. The protein concentrations were quantified using the Coomassie Plus Kit (#23236 Thermo Scientific, Rockford, Ill., USA) according to the protocol of the manufacturer. The diluted samples were transferred into a 96 well plate (#269620, NUNC) and the absorbance was measured at 595 nm using a SpectraMAX Plus plate reader from Molecular Devices. The Protein amount was calculated using the Softmax Pro 5.0 software (Molecular Devices, USA) and then normalized on 1 mg/mL using the corresponding lysis buffer. The normalized samples were further diluted 1:10 using the CSBL1 CeLyA spotting buffer (Zeptosens, cat. No. 9020) supplemented with 1 mM Na-orthovanadate (Sigma, cat No. S-6508). The lysate was transferred to a 96-well V-bottom plate (Fisher Scientific, cat. No. 6067Y), followed by a centrifugation step (5 min, 1500 rpm at 19° C. in an Eppendorf 5810R centrifuge) to remove the unlyzed cell debris.

A MATRIX 2×2 automated pipetting workstation (Thermo Fisher Scientific, UK) was used for reformatting the lysates from the 96-well V-bottom plates to 384-well plates (Greiner, cat. No. 781201). To obtain the desired spotting layout, every sample was diluted to 4 different sample concentrations (d1=100%, d2=75%, d3=50%, d4=25%) by diluting the cell lysate with the corresponding volume of lysis-spotting buffer mix (10% lysis buffer; 90% CSBL1 spotting buffer supplemented with 1 mM Na-orthovanadate.

The samples were spotted onto ZeptoMARK® PWG protein microarray chips (Zeptosens, Witterswil, Switzerland) with the piezoelectric microdispense-based, non-contact Nano-Plotter 2.1 (GeSiM, Grosserkmannsdorf, Germany). Each sample was spotted at 4 different sample concentrations (d1=100%, d2=75%, d3=50%, d4=25%) by diluting the cell lysate with the corresponding volume of spotting-lysis buffer mix. After spotting the ZeptoMARK® protein microarrays, the chips are incubated for 1 hour at 37° C. To receive a uniform blocking result, the CeLyA blocking buffer BB1 (Zeptosens, cat. No. 9040) is administered via an ultrasonic nebulizer. After 20 minutes of blocking the chips are extensively rinsed with deionized water (Milli-Q quality, 18M'Ω×cm) and dried in a nitrogen air flow.

Then, the ZeptoMARK® chips were transferred to the ZeptoCARRIER (Zeptosens, cat. No. 1100), and washed twice with 200 µL CAB1 CeLyA assay buffer (Zeptosens, cat. No. 9032). The assay buffer was then aspirated and each compartment incubated with 100 µL of the primary target antibody (pAkt Ser473 (lot no. 9)(Cell Signaling Technology, Catalog No. 4060); Akt1 pan (lot no. E0401) (Epitomics, Catalog No. 1085-1); Zenon® Alexa Fluor 647 rabbit (Invitrogen, Catalog No. Z25308)) at room temperature (RT) overnight. Post incubation, the primary antibody was removed, the arrays washed twice with CAB1 buffer and further incubated with 100 µL of Alexa fluor 647-labeled anti rabbit IgG Fab fragments (Invitrogen; #Z25305) for one hour at RT in the dark. After incubation, the arrays were washed twice with 200 µL CAB1 buffer. The fluorescence of the target-bound Fab fragments was read out on the ZeptoReader (Zeptosens, Witterswil, Switzerland) using a laser (excitation wavelength 635 nm) and a CCD camera. The fluorescence signal was assessed with exposure times of 1, 3, 5 and 10 seconds, depending on the intensity of the signal. The fluorescence images for each array were analyzed with the ZeptoVIEW Pro 2.0 software (Zeptosens, Witterswil, Switzerland) and the RFI (relative fluorescence intensity) for each signal was calculated.

D. PK-PD Modeling:

Phoenix WinNonlin 6.3 (Pharsight) was used to simulate the mean plasma concentration time profiles after multiple dosing using the non-compartmental nonparametric superposition approach of data generated either from a mouse or rat efficacy study. The predictions are based upon an accumulation ratio computed from the terminal slope (Lambda Z), allowing predictions from simple or complicated dosing schedules.

Statistical Analysis:

Absolute values for primary tumor growth and body weight were used to make the statistical comparisons between groups (one way ANOVA followed by Dunnett's test for normally distributed data; ANOVA on Ranks for not normally distributed data followed by Dunnett's test for equal group size or Dunn's for unequal group size). The significant level was set at p<0.05. Areas under the curve (AUC) recorded for 24 h post last treatment was determined by using the trapezoidal rule method. All statistical calculations were carried out using SigmaStat.

Results

The pre-clinical PK-PD-Efficacy-Tolerability model for Compound A was established following the methods set forth above. For this pre-clinical PK-PD-Efficacy-Tolerability model for Compound A:

Pharmacokinetic Studies and PK Modeling for Compound A:

The pharmacokinetics of Compound A were linear over the range of doses tested (FIG. 1 A: 12.5, 25 and 50 mg/kg qd in nude mice; FIG. 1 B: 12.5, 25, 40 and 80 mg/kg qd in nude rats), and associated with a similar change in AUC between 12.5 and 50 mg/kg in nude mice. A similar relationship was observed in nude rats for doses up to 80 mg/kg. FIGS. 2A and 2B provides a non-parametric superposition model to show the relationship of observed vs. predicted plasma concentrations after oral administration of Compound A at 50 mg/kg qd in nude mice and 40 mg/kg qd in nude rats. (FIGS. 2 A and B). FIGS. 3 A and B provides a comparison of the observed plasma concentrations and model predictions and indicates that this PK model used is very predictive in nude mice ($R^2$=0.99, n=25, p<0.001) at doses below 150 mg/kg qd and nude rats ($R^2$=0.89, n=31, p<0.01) at doses below 100 mg/kg qd. Moreover, FIG. 4A indicates that this PK model used is also predictive to simulate PK profiles Compound A given twice a day (2 qd) in nude mice.

This PK modeling study was repeated to confirm the prior finding that this PK model is predictive to simulate PK profiles of Compound A given twice a day (2 qd) in nude mice. The results of this repeat study are provided in FIG. 4B and re-confirm that this PK model is predictive to simulate PK profiles for Compound A given twice a day (2 qd) in nude mice. This FIG. 4B data is provided herein solely to demonstrate further confirmation of the PK modeling study in nude mice.

PK-PD-Efficacy Modeling

A. Modulation of Phosphorylation of Akt:

The tumor concentrations giving 50% (in vivo $IC_{50}$) and 80% (in vivo $IC_{80}$) S473P-Akt inhibition (0.6 and 4 µmol/L, respectively) versus controls were determined by measuring the level of Akt phosphorylation using RPPA and the specific tumor drug concentration in matched samples from multiple animals (nude mice and rats) and at multiple time points post-treatment with Compound A (FIG. 5). When corrected for plasma protein binding of Compound A in mouse (PPB=91.2%), the in vivo $IC_{50}$ (53 nmol/L) and $IC_{80}$ (352 nmol/L) values roughly approximate the in vitro cellular $IC_{50}$ and $IC_{80}$ of 74 nmol/L and 301 nmol/L respectively.

B. Antitumor Activity of Compound A in the Rat1-myr-p110α Tumor Model:

Compound A was administered orally to Rat1-myr-p110α tumor bearing mice and rats at various doses. Tumor growth inhibition results are summarized below:

| Nude Mice - Dose | Efficacy T/C (observed) | Regression (observed) | Nude Rat Dose | Efficacy T/C (observed) | Regression (observed) |
|---|---|---|---|---|---|
| 6.25 mg qd | 0.19 | — | 6.25 mg qd | 0.22 | — |
| 12.5 mg qd | 0.09 | — | 12.5 mg qd | 0.05 | — |
| 25 mg qd | — | −0.53 | 25 mg qd | — | −0.65 |
| 50 mg qd | — | −0.65 | 50 mg qd | — | −0.80 |
| 6.25 mg 2qd | 0.02 | — | | | |
| 12.5 mg 2qd | — | −0.55 | | | |
| 20 mg 2qd | — | −0.80 | | | |
| 40 mg 2qd | — | −0.86 | | | |

The inhibition appeared to be dose-dependent. Tumor regression was observed at daily doses higher than 25 mg/kg in nude mice and rats and twice-daily doses higher than 12.5 mg/kg in nude mice.

Figure 6:
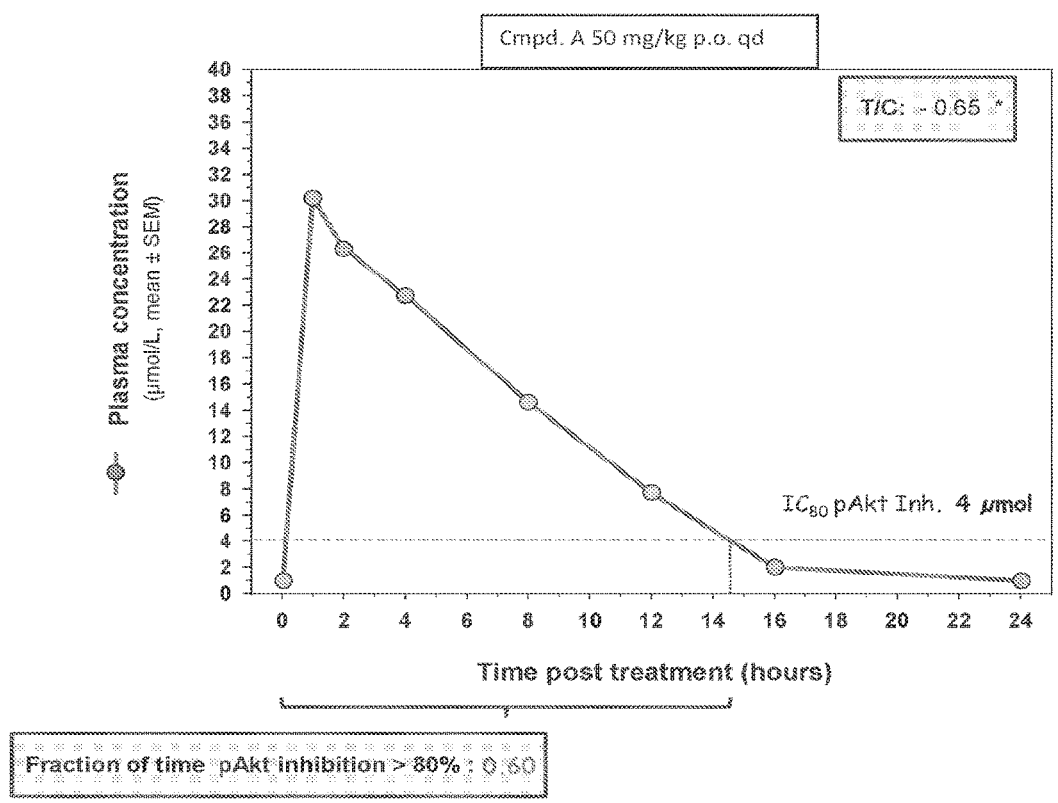
FIG. 6 shows the relationship between exposure, as measured by time over the in vivo IC80 for S473P-Akt inhibition, and anti-tumor efficacy in Rat1-myr P110a tumors treated with Compound A at 50 mg/kg qd.
Figure 7:
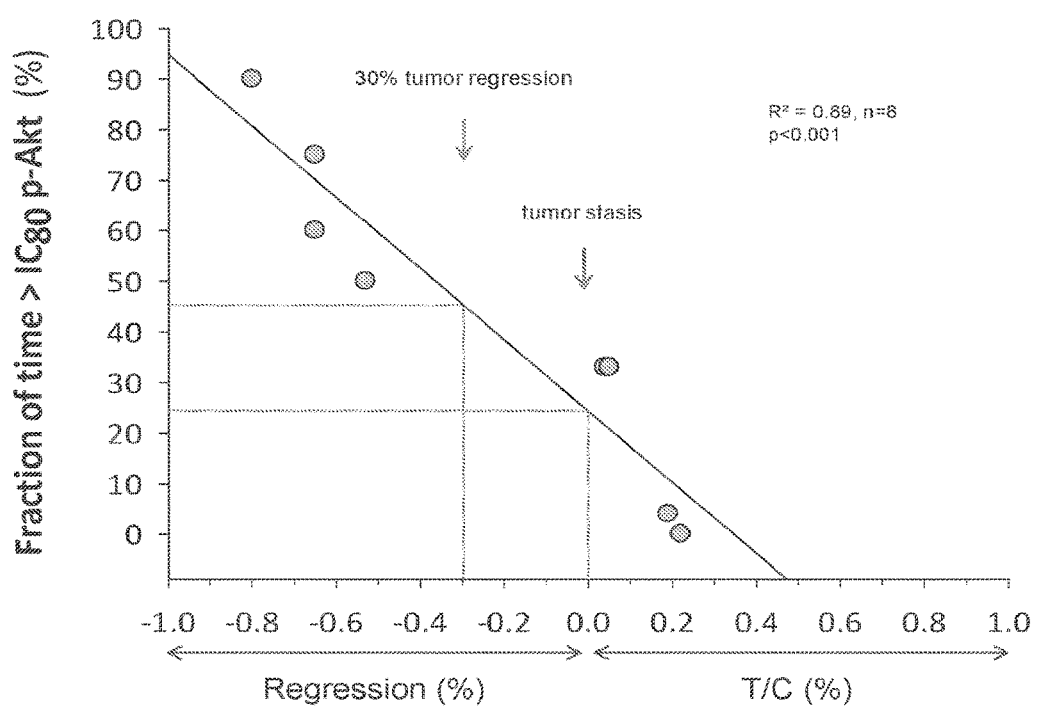
FIG. 7 shows the relationship between the tumor PD marker (pAkt) response and antitumor efficacy observed in mice and rats treated orally qd with various doses of Compound A.

C. PK/PD/Efficacy Relationship:

FIG. 6 provides the relationship between exposure (as measured by time over the in vivo IC80) and anti-tumor efficacy. Further, a nearly linear relationship is identified between the anti-tumor efficacy magnitude and duration of drug exposure (as measured by time over the in vivo $IC_{80}$) over the $IC_{80}$ ($R^2$=0.89; FIG. 7). From this relationship, it has been determined that 80% inhibition of Akt phosphorylation for at least 25% of the dosing interval is required for Compound A to induce tumor stasis, and that this level of pathway inhibition must be sustained for at least 45% of the dosing interval to produce 30% tumor regression.

Figure 8:
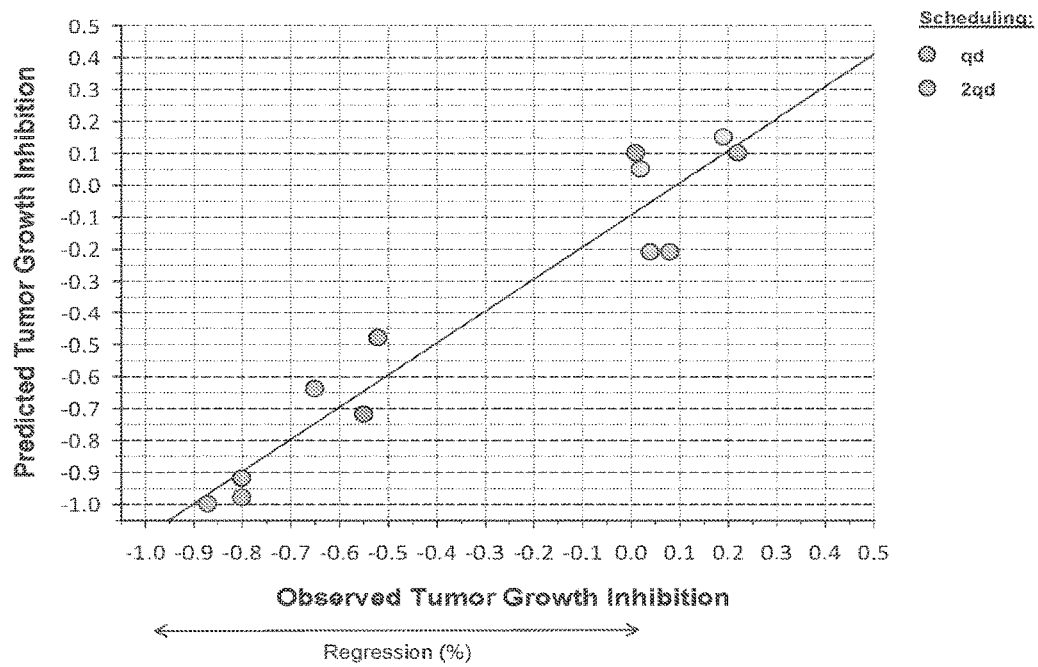
FIG. 8 shows observed versus predicted tumor growth inhibition after oral administration of Compound A from 6.25 to 70 mg/kg on continuous daily schedule at various regimen in nude mice and rats.

FIG. 8 provides a comparison of observed tumor growth inhibition and the model prediction tumor growth inhibition after oral administration of Compound A from 6.25 to 70 mg/kg in qd and 2 qd dosing. Thus, this PK/PD relationship model is predictive of antitumor efficacy of alternative dosing regimens in mice and rats treated orally with various doses of Compound A ($R^2$=0.93, n=12, p<0.001).

PK-PD-Tolerability Modeling

A. Modulation of Glucose and Insulin Levels:

To assess whether Compound A perturbs glucose homeostasis, plasma insulin and glucose blood levels were measured and compared with plasma drug concentrations in matched samples from multiple animals and at multiple time points. In this analysis, insulin plasma levels increased proportionally with Compound A plasma concentrations, while blood glucose levels were maintained close to normal up to 20 μmol/L of Compound A in nude mice (FIGS. 9 A and B) and up to 15 μmol/L of Compound A in nude rats (FIGS. 10 A and B). However, above 20 μmol/L in nude mice and 15 μmol/L in nude rats, a compound concentration-dependent glucose increase which led to hyperglycemia was observed despite insulin plasma level elevation. Thus, the Compound A-related hyperglycemic threshold was defined to be 20 μmol/L and 15 μmol/L in mice and rats, respectively.

Figure 11:
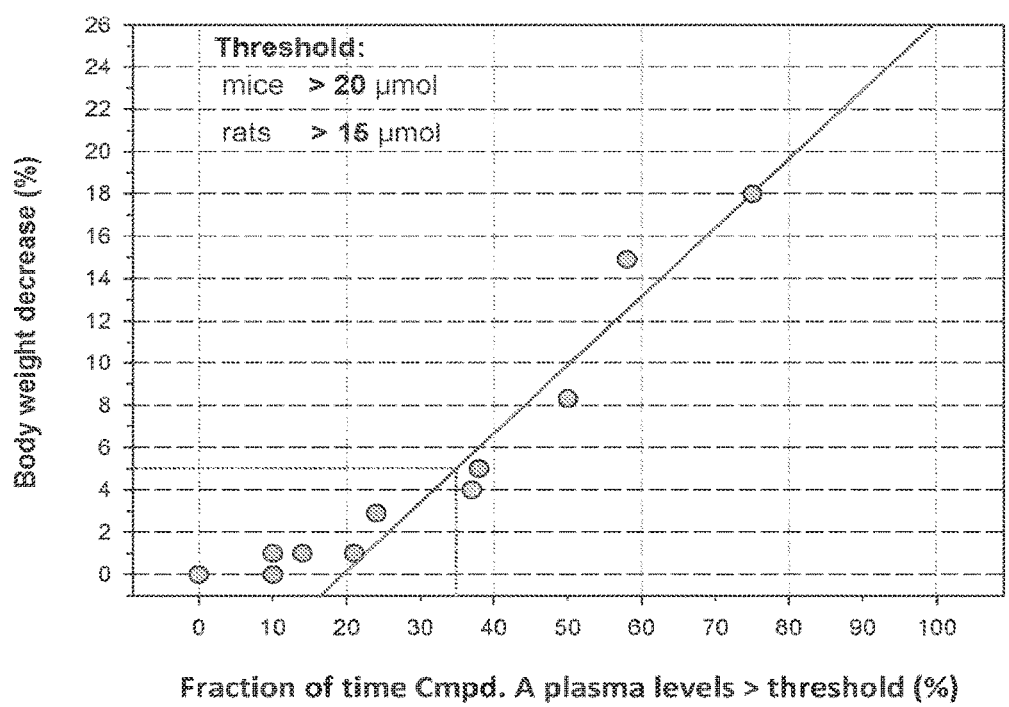
FIG. 11 shows the correlation observed between the fraction of time over plasma hyperglycemia threshold between two consecutive dosing and body weight loss in nude mice and rats.

B. PK/PD/Tolerability Relationship:

Further, a nearly linear relationship was observed between the body weight loss magnitude and duration of exposure above Compound A hyperglycemia threshold (20 μmol/L for nude mice and 15 μmol/L for nude rats; $R^2$=0.98, FIG. 11). From this relationship, it is understood that the compound exposure levels should be sustained for no more than 35% of the dosing interval above the hyperglycemia cut-off to maintain body weight loss below 5% in mice and rats.

PK-PD-Efficacy Modeling

Figure 12:
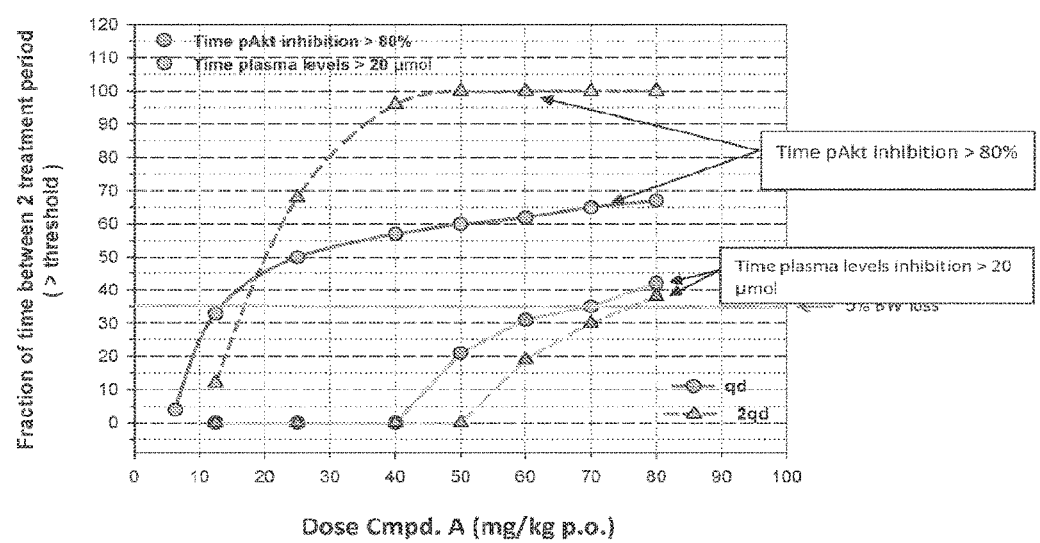
FIG. 12 shows a simulated efficacy curve as determined by the fraction of time above the $IC_{80}$ threshold for S473P-Akt and tolerability curve as determined by the duration of exposure above Compound A hyperglycemia threshold in nude mice treated orally qd or 2 qd on continuous daily schedule with increasing doses of Compound A.
Figure 13:
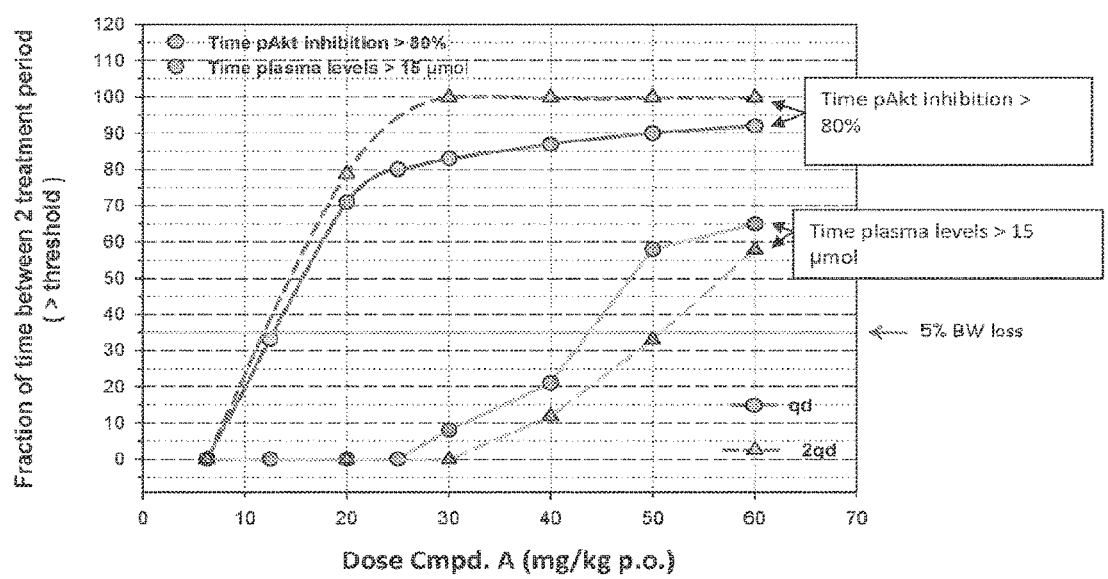
FIG. 13 shows a simulated efficacy curve as determined by the fraction of time above the $IC_{80}$ threshold for S473P-Akt and tolerability curve as determined by the duration of exposure above Compound A hyperglycemia threshold in nude rats treated orally qd or 2 qd with increasing doses of Compound A.

Simulated efficacy curves (as determined by the fraction of time above the $IC_{80}$ threshold for 5473P-Akt) and tolerability curves (as determined by the duration of exposure above Compound A hyperglycemia threshold (20 μmol/L)) in mice treated orally qd with increasing doses of Compound A are shown in the graph at FIG. 12. The modeling suggests that at the dose of 70 mg/kg qd (less than 5% BW loss), 80% pAkt inhibition will be achieved for 65% of the time between two consecutive treatments leading to 55% tumor regression (FIG. 12, FIG. 7). If the dose of 70 mg/kg qd is given as 35 mg/kg twice a day (2 qd), the model tells us that 80% pAkt inhibition will be achieved for 100% of the time between two consecutive treatments leading to tumor regression. In nude rats were the hyperglycemia threshold was set to 15 μmol/L, the dose of 30 mg/kg qd (no BW loss) will lead to 80% pAkt inhibition for 83% of the time between two consecutive treatments leading to 80% tumor regression (FIG. 13, FIG. 7).

Case Study: 20 mg/kg qd in "ALTERNATIVE SCHEDULE 1" Dosing Regimen in Nude Rats

Based upon the foregoing analysis, the pre-clinical PK-PD-Efficacy-Tolerability modeling for Compound A described above is a valuable tool to predict efficacy and tolerability of the following dosing schedule of Compound A: oral administration of Compound A once per day (q.d.) or twice per day (b.i.d.) for five-consecutive days followed by no administration of Compound A for two days (CYCLE 1), and then a repeat of the same dosing regimen [i.e, oral administration of Compound A once per day (q.d.) or twice per day (b.i.d.) for five-consecutive days, followed by no administration of Compound A for two days] in one or more subsequent cycles. This alternative dosing schedule is referred to as "ALTERNATIVE SCHEDULE 1". As described herein, this model is here used to explore and guide dose scheduling in clinical studies.

Figure 15:
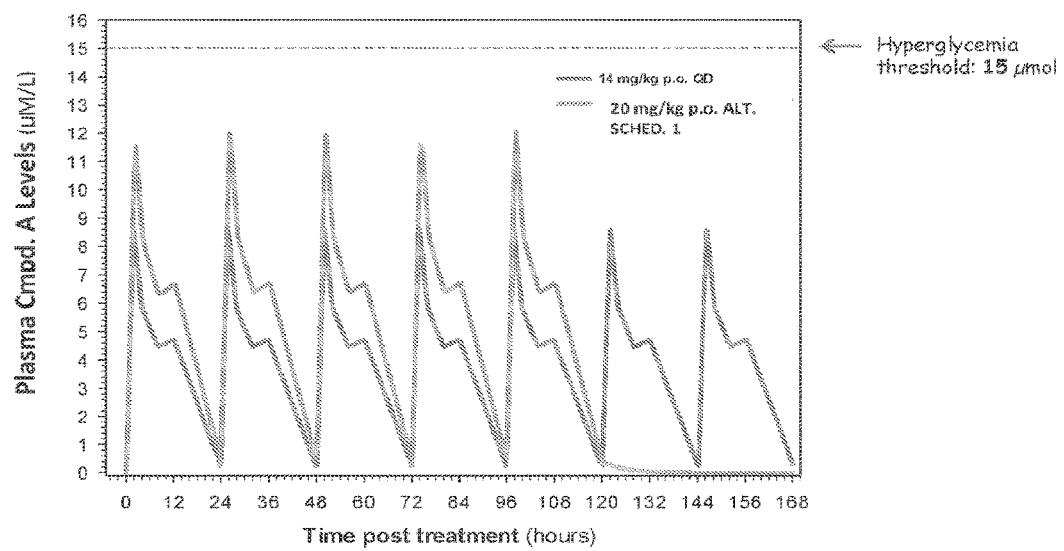
FIG. 15 shows a simulated plasma PK profiles in nude rats treated orally with Compound A at 20 mg/kg in ALTERNATIVE SCHEDULE 1, as defined in Example 1, or 14 mg/kg qd in continuous daily schedule.

FIG. 14 provides graphs showing the simulated efficacy of Compound A in Rat1-myr P110α tumor bearing nude rats orally with COMPOUND A at 20 mg/kg in ALTERNATIVE SCHEDULE 1 (A) as compared to 14 mg/kg qd in continuous daily schedule (ie., with no drug holiday) (B). FIG. 15 provides the simulated plasma PK profile in Rat1-myr P110α tumor bearing nude rats orally with COMPOUND A at 20 mg/kg in ALTERNATIVE SCHEDULE 1 as compared to 14 mg/kg qd in continuous daily schedule (ie., with no drug holiday).

Based on our model simulation (FIG. 7), ALTERNATIVE SCHEDULE 1 for Compound A can (a) achieve similar or improved anti-tumor efficacy observed in nude rats orally administered Compound A once each day (q.d.) on a continuous daily schedule and (b) achieve at least partial regression (30% tumor regression) over the entire treatment period if Compound A plasma concentration is above the $IC_{80}$ on pAkt for 45% of the time between two treatment periods. Based on equivalent AUC, the human dose for Compound A of 300-350 mg/day p.o. (Cmax: 3500 ng/ml=8 µmol/L; AUC: 35000 h.ng/ml=80 h·µmol/L) corresponds to a 20 mg/kg ALTERNATIVE SCHEDULE 1 p.o. dose in nude rats. The corresponding total dose for qd in continuous daily schedule p.o. dose would be 14 mg/kg.

According to this model in nude rats (FIG. 13), Compound A at 20 mg/kg will result in approximately 60% tumor regression. Thus, predicted efficacy of 20 mg/kg in ALTERNATIVE SCHEDULE 1 in nude rats is presented in FIG. 14 A. Max efficacy is 60% regression with a recovery to 30% regression at the end of the 2 days of drug holidays. Predicted efficacy for the 14 mg/kg daily dosing is continuous 30% tumor regression (FIG. 14 B).

The predicted Compound A plasma levels following oral treatment in mice and rats with 14 mg qd in continuous daily schedule or 20 mg in ALTERNATIVE SCHEDULE 1 will not exceed 15 µmol (Hyperglycemia threshold). (FIG. 15)

Assuming that the relationship between PD and efficacy is similar in humans and xenografts, this model and analysis may be useful to predict tumor response in humans to ALTERNATIVE SCHEDULE 1.

What is claimed is:

1. A method of treating a breast cancer in a patient in need thereof, comprising orally administering a therapeutically effective amount of the compound of formula (I)

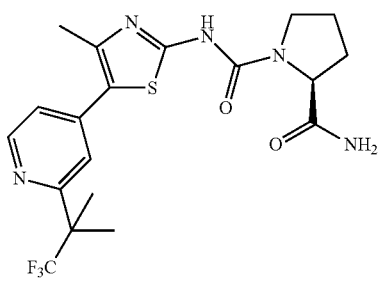

(I)

or a pharmaceutically acceptable salt thereof to the patient in a daily dose of about 100 mg to about 450 mg for at least two five-consecutive day cycles, wherein said compound or a pharmaceutically acceptable salt thereof is not administered to the patient for a period of about 2 days between one five-consecutive day cycle and its subsequent five-consecutive day cycle.

2. A method of treating a breast cancer comprising first administering to a patient in need thereof a compound of formula (I) according to claim 1 or a pharmaceutically acceptable salt thereof in amount of about 100 mg to about 450 mg daily on a continuous daily schedule via oral administration, second determining said patient has a side effect selected from neutropenia, elevated bilirubin, cardiac toxicity, unstable angina, myocardial infarction, persistent hypertension, peripheral sensory or motor neuropathy/pain, hepatic dysfunction, reduced red and/or white blood cell count, hyperglycemia, nausea, decreased appetite, diarrhea, rash and hypersensitivity, photosensitivity, asthenia/fatigue, vomiting, stomatitis, oral mucositis, pancreatitis, dysgeusia, and dyspepsia after administration of said compound of formula (I) or a pharmaceutically acceptable salt thereof to said patient, and third reducing the administration of said compound of formula (I) or a pharmaceutically acceptable salt thereof to a daily dose of about 100 mg to about 450 mg via oral administration for at least two five-consecutive day cycles via oral administration, wherein said compound or a pharmaceutically acceptable salt thereof is not administered to the patient for a period of about 2 days between one five-consecutive day cycle and its subsequent five-consecutive day cycle.

3. A method according to claim 1, wherein the daily dose of the compound of formula (I) or a pharmaceutically acceptable salt thereof is about 200 mg to about 400 mg.

4. A method according to claim 1, wherein the compound of formula (I) or a pharmaceutically acceptable salt is orally administered once per day (q.d.) in a daily dose of about 100 mg to about 450 mg for at least two five-consecutive day cycles.

5. A method according to claim 2, wherein the compound of formula (I) or a pharmaceutically acceptable salt thereof is administered in two or more of said five-consecutive day cycles until the relief, reduction, or alleviation of the severity, occurrence rate, or frequency of at least one side effect in said patient, and wherein the side effect is hyperglycemia.

* * * * *